United States Patent [19]

Hoefle et al.

[11] Patent Number: 4,647,576

[45] Date of Patent: Mar. 3, 1987

[54] TRANS-6-[2-(SUBSTITUTEDPYRROL-1-YL)ALKYL]-PYRAN-2-ONE INHIBITORS OF CHOLESTEROL SYNTHESIS

[75] Inventors: Milton L. Hoefle; Bruce D. Roth; Charlotte D. Stratton, all of Ann Arbor, Mich.

[73] Assignee: Warner-Lambert Company, Morris Plains, N.J.

[21] Appl. No.: 679,676

[22] Filed: Dec. 10, 1984

Related U.S. Application Data

[63] Continuation-in-part of Ser. No. 653,798, Sep. 24, 1984, abandoned.

[51] Int. Cl.$^4$ .................. C07D 405/06; A61K 31/40
[52] U.S. Cl. .................................. 514/422; 514/343; 548/517; 548/562; 548/515; 548/465; 548/453; 546/281; 546/270; 546/271; 546/272; 544/236
[58] Field of Search .............. 548/517, 562; 514/422, 514/343; 546/281

[56] References Cited

U.S. PATENT DOCUMENTS

| | | | |
|---|---|---|---|
| 3,983,140 | 9/1976 | Endo et al. | 549/292 |
| 4,198,425 | 4/1980 | Mistui et al. | 514/460 |
| 4,219,560 | 8/1980 | Houlihan | 544/372 X |
| 4,248,889 | 2/1981 | Oka et al. | 514/532 |
| 4,255,444 | 3/1981 | Oka et al. | 549/292 X |
| 4,308,378 | 12/1981 | Stokker | 549/292 |
| 4,343,811 | 8/1982 | Humaus et al. | 514/415 |
| 4,351,844 | 9/1982 | Patchett et al. | 514/460 |
| 4,375,425 | 3/1983 | Willard et al. | 549/292 X |
| 4,376,863 | 3/1983 | Lam | 549/292 |
| 4,440,927 | 4/1984 | Prugh | 549/292 |

FOREIGN PATENT DOCUMENTS

895445  4/1983  Belgium .

OTHER PUBLICATIONS

Hulcher, Archives of Biochemistry and Biophysics, 146, (1971), pp. 422–427.

Primary Examiner—Donald G. Daus
Assistant Examiner—William A. Teoli, Jr.
Attorney, Agent, or Firm—Jerry F. Janssen

[57] ABSTRACT

6-[2-(Substituted–pyrrol-1-yl)aklyl]pyran-2-ones and the corresponding ring-opened hydroxy-acids derived therefrom are potent inhibitors of the enzyme 3-hydroxy-3-methylglutarylcoenzyme A reductase (HMG-CoA reductase), and are thus useful hypolipidemic and hypocholesterolemic agents. Pharmaceutical compositions containing such compounds, and a method of treatment employing such pharmaceutical compositions are also disclosed.

19 Claims, No Drawings

4,647,576

TRANS-6-[2-(SUBSTITUTEDPYRROL-1-YL)ALKYL]-PYRAN-2-ONE INHIBITORS OF CHOLESTEROL SYNTHESIS

CROSS-REFERENCE TO RELATED APPLICATIONS

This application is a continuation-in-part of copending application Ser. No. 653,798 filed Sept. 24, 1984 abandoned.

BACKGROUND OF THE INVENTION

The present invention is related to compounds and pharmaceutical compositions useful as hypocholesterolemic and hypolipidemic agents. More particularly, this invention concerns certain trans-6-[2-(substitutedpyrrol-1-yl)alkyl]-2-ones and the corresponding ring-opened acids derived therefrom which are potent inhibitors of the enzyme 3-hydroxy-3-methylglutaryl-coenzyme A reductase (HMG-CoA reductase), pharmaceutical composition containing such compounds, and a method of lowering blood serum cholesterol levels employing such pharmaceutical compositions.

High levels of blood cholesterol and blood lipids are conditions which are involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine* (1981), 305, No. 9, 515–517). It has now been established that lowering LDL-C levels affords protection from coronary heart disease (cf. *Journal of the American Medical Association* (1984) 251, No. 3, 351–374).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer et al., *Proc. Soc. Exper. Biol. Med.* (1959), 102, 270) and F. H. Hulcher, *Arch. Biochem. Biophys.* (1971), 146, 422.

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown et al., *J. Chem. Soc. Perkin I*, (1976), 1165.

U.S. Pat. No. 4,255,444 to Oka et al. discloses several synthetic derivatives of mevalonolactone having antilipidemic activity.

U.S. Pat. Nos. 4,198,425 and 4,262,013 to Mitsue et al. disclose aralkyl derivatives of mevalonolactone which are useful in the treatment of hyperlipidemia.

U.S. Pat. No. 4,375,475 to Willard et al. discloses certain substituted 4-hydroxytetrahydropyran-2-ones which, in the 4(R)-trans stereoisomeric form, are inhibitors of cholesterol biosynthesis.

SUMMARY OF THE INVENTION

In accordance with the present invention, there are provided certain trans-6-[2-(substitutedpyrrol-1-yl)alkyl]pyran-2-ones and the corresponding ring-opened hydroxy-acids derived therefrom which are potent inhibitors of cholesterol biosynthesis by virtue of their ability to inhibit the enzyme 3-hydroxy-3-methylglutarylcoenzyme A reductase (HMG-CoA reductase).

In particular, in its broadest chemical compound aspect, the present invention provides compounds of structural formula I

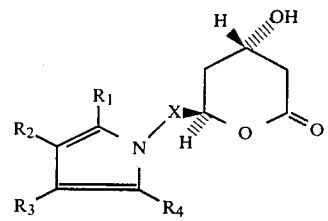

wherein X is $-CH_2-$, $-CH_2CH_2-$, or $-CH(CH_3)CH_2-$. $R_1$ is 1-naphthyl; 2-naphthyl; cyclohexyl; norbornenyl; phenyl; phenyl substituted by fluorine, chlorine, hydroxy, trifluoromethyl, alkyl of from one to four carbon atoms, alkoxy of from one to four carbon atoms, or alkanoyloxy of from two to eight carbon atoms; 2-, 3-, or 4-pyridinyl; 2-, 3-, or 4-pyridinyl-N-oxide; or

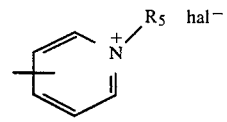

where $R_5$ is alkyl of from one to four carbon atoms and hal$^-$ is chloride, bromide, or iodide. $R_2$ and $R_3$ are independently hydrogen; chlorine; bromine; cyano; trifluoromethyl; phenyl; alkyl of from one to four carbon atoms; carboalkoxy of from two to eight carbon atoms; $-CH_2OR_6$ where $R_6$ is hydrogen, alkanoyl of from one to six carbon atoms, or where $R_2$ and $R_3$ are $-CH_2OCONHR_7$ where $R_7$ is alkyl of from one to six carbon atoms, phenyl, or phenyl substituted with chlorine, bromine, or alkyl of from one to four carbon atoms. $R_2$ and $R_3$ may also, when taken together with the carbon atoms to which they are attached, form a ring denoted by

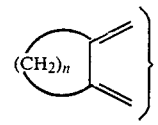

where n is three or four; a ring denoted by

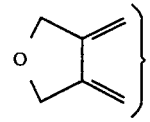

a ring denoted by

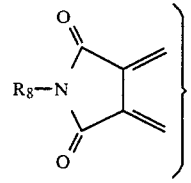

where $R_8$ is hydrogen, alkyl of from one to six carbon atoms, phenyl, or benzyl; or a ring denoted by

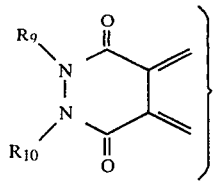

where $R_9$ and $R_{10}$ are hydrogen, alkyl of from one to four carbon atoms, or benzyl.

$R_4$ is alkyl of from one to four carbon atoms, cyclopropyl, cyclobutyl, or trifluoromethyl.

Also contemplated as falling within this aspect of the invention are the corresponding dihydroxy-acid compounds of formula II corresponding to the opened form of the lactone ring of compounds of formula I

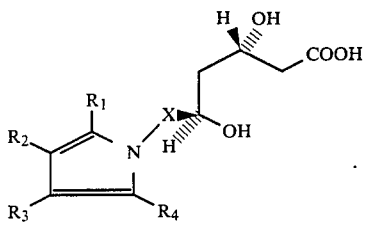

where X, $R_1$, $R_2$, $R_3$, and $R_4$ are as defined above, and the pharmaceutically acceptable salts thereof, all of the compounds being in the trans racemate of the tetrahydropyran moiety.

In another aspect of the present invention, there is provided a method of preparing compounds of formula I above by (a) first reacting a substituted [(pyrrol-1-yl)alkyl]aldehyde compound of formula III

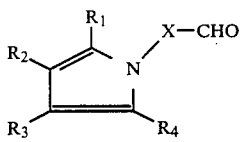

where X, $R_1$, $R_2$, $R_3$, and $R_4$ are as defined above, with the alkali metal salt of the dianion of methyl acetoacetate to form a compound of structural formula IV

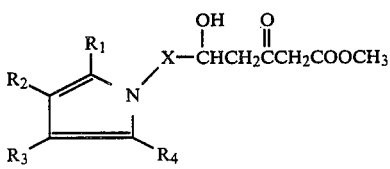

where X, $R_1$, $R_2$, $R_3$, and $R_4$ are as defined above, then successivly (b) reducing compound IV with a trialkylborane and sodium borohydride and (c) oxidizing with alkaline hydrogen peroxide to produce an acid compound of formula V

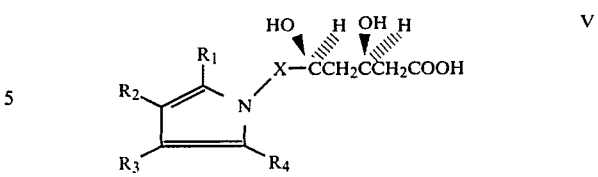

and finally (d) cyclizing, if desired, the acid compound of formula V to a lactone compound of formula I by heating in an inert solvent or, alternatively converting, if desired, the acid compound of formula V to a pharmaceutically acceptable salt.

In another aspect, the present invention provides pharmaceutical compositions, useful as hypolipidemic or hypocholesterolemic agents, comprising a hypolipidemic or hypocholesterolemic affective amount of a compound in accordance with this invention as set forth above, in combination with a pharmaceutically acceptable carrier.

In another aspect, the present invention provides a method of inhibiting cholesterol biosynthesis in a patient in need of such treatment by administering a pharmaceutical composition in accordance with the present invention as defined above.

DETAILED DESCRIPTION

In a first preferred subgeneric chemical compound aspect, the present invention provides compounds of formula I above wherein X is $-CH_2CH_2-$, $R_1$ is as defined above, $R_2$ and $R_3$ are independently hydrogen, chlorine, or bromine, and $R_4$ is as defined above.

In a second preferred subgeneric chemical compound aspect, the present invention provides compounds of formula I above where X is $-CH_2CH_2-$, $R_1$ is phenyl or phenyl substituted by fluorine, chlorine, hydroxy, trifluoromethyl, alkyl of from one to four carbon atoms, alkoxy of from one to four carbon atoms, or alkanoyloxy of from two to eight carbon atoms, or where $R_1$ is 2-, 3-, or 4-pyridinyl; 2-, 3-, or 4-pyridinyl-N-oxide, or

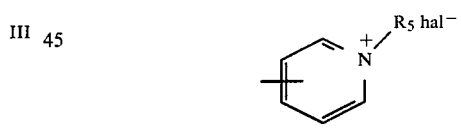

where $R_5$ is alkyl of from one to four carbon atoms and hal$^-$ is chloride, bromide, or iodide. In this aspect of the invention, $R_2$ and $R_3$ are preferably independently hydrogen, chlorine, or bromine, and $R_4$ is alkyl of from one to four carbon atoms or trifluoromethyl.

In a third preferred subgeneric chemical compound aspect, the present invention provides compounds of formula I above where X is $-CH_2CH_2-$, $R_1$ is phenyl or phenyl substituted by fluorine, chlorine, hydroxy, trifluoromethyl, alkoxy of from one to four carbon atoms, or alkanoyloxy of from two to eight carbon atoms, $R_2$ and $R_3$ are independently hydrogen, chlorine, or bromine, and $R_4$ is isopropyl or trifluoromethyl.

In a fourth preferred subgeneric chemical compound aspect, the present invention provides compounds of formula I above where X is $-CH_2CH_2-$, and $R_1$ is phenyl or phenyl substituted by fluorine, chlorine, trifluoromethyl, alkyl of from one to four carbon atoms, alkoxy of from one to four carbon atoms, or alkanoyloxy of from two to eight carbon atoms, or where $R_1$ is 1-naphthyl, or 2-naphthyl. In this preferred aspect of the invention, $R_2$ and $R_3$ are independently hydrogen, chlorine, bromine, cyano, trifluoromethyl, phenyl, alkyl of from one to four carbon atoms, carboalkoxy of from two to eight carbon atoms, —$CH_2OR_6$ where $R_6$ is hydrogen or alkanoyl of from one to six carbon atoms, —$CH_2OCONHR_7$ where $R_7$ is alkyl of from one to six carbon atoms, phenyl, or phenyl substituted with chlorine, bromine, or alkyl of from one to four carbon atoms. In this aspect of the invention, $R_2$ and $R_3$ may also, when taken together with the carbon atoms to which they are attached, form a ring denoted by

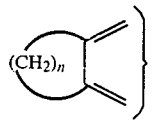

where n is three or four; a ring denoted by

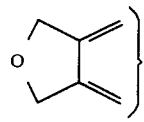

a ring denoted by

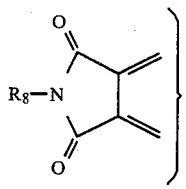

where $R_8$ is hydrogen, alkyl of from one to four carbon atoms, phenyl, or benzyl; or a ring denoted by

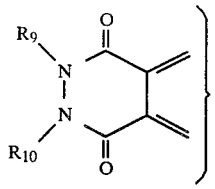

where $R_9$ and $R_{10}$ are hydrogen, alkyl of from one to four carbon atoms, or benzyl. In this aspect of the invention, $R_4$ is preferably alkyl of from one to four carbon atoms, cyclopropyl, cyclobutyl, or trifluoromethyl.

In a fifth preferred subgeneric chemical compound aspect, the present invention provides compounds of formula I above where X is —$CH_2CH_2$—, and $R_1$ is phenyl or phenyl substituted by fluorine, chlorine, trifluoromethyl, alkyl of from one to four carbon atoms, alkoxy of from one to four carbon atoms, or alkanoyloxy of from two to eight carbon atoms. $R_2$ and $R_3$ are preferably independently hydrogen, chlorine, bromine, phenyl, or carboalkoxy of from two to eight carbon atoms. In this aspect of the invention $R_2$ and $R_3$ may also, when taken together with the carbon atoms to which they are attached, form a ring denoted by

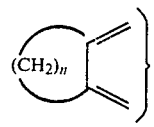

where n is three or four; a ring denoted by

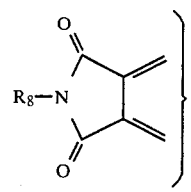

where $R_8$ is hydrogen, or alkyl of from one to four carbon atoms; or a ring denoted by

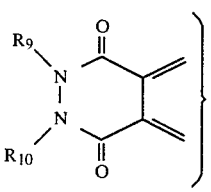

where $R_9$ and $R_{10}$ are hydrogen or alkyl of from one to four carbon atoms. In this aspect of the invention, $R_4$ is preferably alkyl of from one to four carbon atoms, or trifluoromethyl.

In a sixth preferred subgeneric chemical compound aspect, the present invention provides compounds of formula I above where X is —$CH_2CH_2$—, $R_1$ is is phenyl or phenyl substituted by fluorine, chlorine, trifluormethyl, alkyl of from one to four carbon atoms, alkoxy of from one to four carbon atoms, or alkanoyloxy of from two to eight carbon atoms. $R_2$ and $R_3$ are preferably independently carboalkoxy of from two to eight carbon atoms or, when taken together with the carbon atoms to which they are attached form a ring denoted by

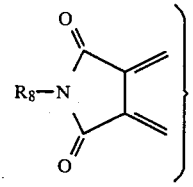

where $R_8$ is hydrogen or alkyl of from one to four carbon atoms. In this aspect of the invention, $R_4$ is preferably isopropyl or trifluoromethyl.

As used throughout this specification and the appended claims, the term "alkyl" denotes a branched or unbranched saturated hydrocarbon group derived by the removal of one hydrogen atom from an alkane.

The term "alkoxy" denotes an alkyl group, as just defined, attached to the parent molecular residue through an oxygen atom.

The term "alkanoyloxy" is meant to denote an alkyl group, as defined above, attached to a carbonyl group and thence, through an oxygen atom, to the parent molecular residue.

The term "carboalkoxy" is meant to denote an alkyl group, as defined above, attached to an oxygen atom and thence, through a carbonyl group, to the parent molecular residue.

The term "norbornenyl" denotes a group derived by the removal of a hydrogen atom (other than at a bridgehead carbon atom) from bicyclo[2.2.1]hept-2-ene.

Specific examples of compounds contemplated as falling within the scope of the present invention include the following:

trans-6-[2-[2-Cyclobutyl-5-(4-fluorophenyl)-1H-pyrrol-1-yl]ethyl]tetrahydro-4-hydroxy-2H-pyran-2-one.
trans-6-[2-[2-Cyclohexyl-5-(4-fluorophenyl)-1H-pyrrol-1-yl]ethyl]tetrahydro-4-hydroxy-pyran-2-one.
trans-Tetrahydro-4-hydroxy-6-[2-(2-methyl-5-phenyl-1H-pyrrol-1-yl)ethyl]-2H-pyran-2-one.
trans-6-[2-[2-(4-Chlorophenyl)-5-methyl-1H-pyrrol-1-yl]ethyl]tetrahydro-4-hydroxy-2H-pyran-2-one.
trans-Tetrahydro-4-hydroxy-6-[2-[2-(4-methoxyphenyl)-5-methyl-1H-pyrrol-1-yl]ethyl]-2H-pyran-2-one.
trans-6-[2-[2-([1,1'-Biphenyl]-4-yl)-5-methyl-1H-pyrrol-1-yl]ethyl]tetrahydro-4-hydroxy-2H-pyran-2-one.
trans-Tetrahydro-4-hydroxy-6-[2-[2-methyl-5-[3-(trifluoromethyl)phenyl]-1H-pyrrol-1-yl]ethyl]-2H-pyran-2-one.
trans-6-[2-[2-(2,5-Dimethylphenyl)-5-(1-methylethyl)-1H-pyrrol-1-yl]ethyl]tetrahydro-4-hydroxy-2H-pyran-2-one.
trans-6-[2-[2-(2,6-Dimethoxyphenyl)-5-(1-methylethyl)-1H-pyrrol-1-yl]ethyl]tetrahydro-4-hydroxy-2H-pyran-2-one.
trans-Tetrahydro-4-hydroxy-6-[2-[2-methyl-5-(2-naphthalenyl)-1H-pyrrol-1-yl]ethyl]-2H-pyran-2-one.
trans-6-[2-(2-(Cyclohexyl-5-trifluoromethyl-1H-pyrrol-1-yl)ethyl]tetrahydro-4-hydroxy-2H-pyran-2-one.
trans-6-[2-[2-(4-Fluorophenyl)-3,4-dimethyl-5-(1-methylethyl)-1H-pyrrol-1-yl]ethyl]tetrahydro-4-hydroxy-2H-pyran-2-one.
trans-2-(4-Fluorophenyl)-5-(1-methylethyl)-1-[2-(tetrahydro-4-hydroxy-6-oxo-2H-pyran-2-yl)ethyl]-1H-pyrrole-3,5-dicarboxylic acid.
trans-2-(4-Fluorophenyl)-N³,N³,N⁴,N⁴-tetramethyl-5-(1-methylethyl)-1-[2-(tetrahydro-4-hydroxy-6-oxo-2H-pyran-2-yl)ethyl]-1H-pyrrole-3,4-dicarboxamide.
trans-6-[2-[3,4-Dichloro-2-(3-fluorophenyl)-5-(1-methylethyl)-1H-pyrrol-1-yl]ethyl]tetrahydro-4-hydroxy-2H-pyran-2-one.
trans-2-(4-Fluorophenyl)-5-(1-methylethyl)-1-[2-(tetrahydro)-4-hydroxy-6-oxo-2H-pyran-2-yl)ethyl]-1H-pyrrole-3,4-dicarbonitrile.
trans-6-[2-[3,4-Diacetyl-2-(4-fluorophenyl)-5-(1-methylethyl)-1H-pyrrol-1-yl]ethyl]tetrahydro-4-hydroxy-2H-pyran-2-one.
trans-Diethyl 2-(4-Fluorophenyl)-1-[2-(tetrahydro)-4-hydroxy-6-oxo-2H-pyran-2-yl)ethyl]-5-(trifluoromethyl)-1H-pyrrole-3,4-dicarboxylate.
trans-Bis(1-methylethyl) 2-(4-Fluorophenyl)-5-(1-methylethyl)-1-[2-(tetrahydro)-4-hydroxy-6-oxo-2H-pyran-2-yl)ethyl]-1H-pyrrole-3,4-dicarboxylate.
trans-6-[2-[3,4-Diethyl-2-(4-fluorophenyl)-5-(1-methylethyl)-1H-pyrrol-1-yl]ethyl]tetrahydro-4-hydroxy-2H-pyran-2-one.
trans-6-[2-[2-(4-Fluorophenyl)-3,4-bis(hydroxymethyl)-5-(1-methylethyl)-1H-pyrrol-1-yl]-ethyl]tetrahydro-4-hydroxy-2H-pyran-2-one.
trans-1-Methylethyl 4-Chloro-2-(4-fluorophenyl)-5-(1-methylethyl)-1-[2-(tetrahydro)-4-hydroxy-6-oxo-2H-pyran-2-yl)ethyl]-1H-pyrrole-3-carboxylate.
trans-6-[2-[4-(4-Fluorophenyl)-6-(1-methylethyl)-1H-furo[3,4-c]pyrrol-5(3H)-yl]ethyl]tetrahydro-4-hydroxy-2H-pyran-2-one.
trans-6-[2-[2-(4-Fluorophenyl)-5-(1-methylethyl)-3,4-bis[[[(phenylamino)carbonyl]oxy]methyl]-1H-pyrrol-1-yl]ethyl]tetrahydro-4-hydroxy-2H-pyran-2-one.
trans-1-Methylethyl 4-Chloro-5-(4-fluorophenyl)-2-(1-methylethyl)-1-[2-(tetrahydro)-4-hydroxy-6-oxo-2H-pyran-2-yl)ethyl]-1H-pyrrole-3-carboxylate.
trans-Ethyl 5-(4-Fluorophenyl)-1-[2-(tetrahydro)-4-hydroxy-6-oxo-2H-pyran-2-yl)ethyl]-2-(trifluoromethyl)-1H-pyrrole-3-carboxylate.
trans-Ethyl 5-(4-Fluorophenyl)-2-(1-methylethyl)-4-phenyl-1-[2-(tetrahydro-4-hydroxy-6-oxo-2H-pyran-2-yl)ethyl]-1H-pyrrole-3-carboxylate.
trans-6-[2-[1-(4-Fluorophenyl)-4,5,6,7-tetrahydro-3-methyl-2H-isoindol-2-yl]ethyl]tetrahydro-4-hydroxy-2H-pyran-2-one.
trans-4-(4-Fluorophenyl)-2-methyl-6-(1-methylethyl)-5-[2-(tetrahydro-4-hydroxy-6-oxo-2H-pyran-2-yl)ethyl]-pyrrolo[3,4-c]pyrrole-1,3(2H,5H)-dione.
trans-6-[2-[1-(4-Fluorophenyl)-5,6-dihydro-3-(1-methylethyl)pyrrolo[3,4-c]pyrrol-2(4H)-yl]ethyl]-tetrahydro-4-hydroxy-2H-pyran-2-one.
trans-6-[2-[1-(4-Fluorophenyl)-5,6-dihydro-5-methyl-3-(1-methylethyl)pyrrolo[3,4-c]pyrrol-2(4H)-yl]-ethyl]-tetrahydro-4-hydroxy-2H-pyran-2-one.
trans-6-[2-[3-Chloro-5-(4-fluorophenyl)-2-(1-methylethyl)-4-phenyl-1H-pyrrol-1-yl]ethyl]tetrahydro-4-hydroxy-2H-pyran-2-one.
trans-6-[2-[2-(4-Fluorophenyl)-5-(1-methylethyl)-3,4-diphenyl-1H-pyrrol-1-yl]ethyl]tetrahydro-4-hydroxy-2H-pyran-2-one.

Particularly preferred compounds in accordance with the present invention are:

trans-6-[2-[3,4-Dichloro-2-(4-fluorophenyl)-5-(1-methylethyl)-1H-pyrrol-1-yl]ethyl]tetrahydro-4-hydroxy-2H-pyran-2-one.
trans-6-[2-[3,4-Dibromo-2-(4-fluorophenyl)-5-(1-methylethyl)-1H-pyrrol-1-yl]ethyl]tetrahydro-4-hydroxy-2H-pyran-2-one.
trans-6-[2-[2-(4-Fluorophenyl)-5-(trifluoromethyl)-1H-pyrrol-1-yl]ethyl]tetrahydro-4-hydroxy-2H-pyran-2-one.
trans-Dimethyl 2-(4-Fluorophenyl)-5-(1-methylethyl)-1-[2-(tetrahydro-4-hydroxy-6-oxo-2H-pyran-2-yl)ethyl]-1H-pyrrole-3,4-dicarboxylate.
trans-6-[2-[2-(4-Fluorophenyl-5-methyl-1H-pyrrol-1-yl]ethyl]tetrahydro-4-hydroxy-2H-pyran-2-one.
trans-6-[2-[2-(4-Fluorophenyl)-5-(1-methylethyl)-1H-pyrrol-1-yl]ethyl]tetrahydro-4-hydroxy-2H-pyran-2-one.
trans-6-[2-[2-Cyclopropyl-5-(4-fluorophenyl)-1H-pyrrol-1-yl]ethyl]tetrahydro-4-hydroxy-2H-pyran-2-one.
trans-6-[2-[2-(1,1-Dimethylethyl)-5-(4-fluorophenyl)-1H-pyrrol-1-yl]ethyl]tetrahydro-4-hydroxy-2H-pyran-2-one.
trans-Tetrahydro-4-hydroxy-6-[2-[2-(2-methoxyphenyl)-5-trifluoromethyl-1H-pyrrol-1-yl]ethyl]-2H-pyran-2-one.
trans-Tetrahydro-4-hydroxy-6-[2-[2-(2-methoxyphenyl)-5-(1-methylethyl)-1H-pyrrol-1-yl]ethyl]-2H-pyran-2-one.
trans-Tetrahydro-4-hydroxy-6-[2-[2-methyl-5-(1-naphthalenyl)-1H-pyrrol-1-yl]ethyl]-2H-pyran-2-one.

trans-6-[2-(2-Bicyclo[2.2.1]hep-5-en-2-yl-5-methyl-1H-pyrrol-1-yl)ethyl]tetrahydro-4-hydroxy-2H-pyran-2-one.

trans-6-[2-[2-(4-Fluorophenyl)-5-(1-methylphenyl)-1H-pyrrol-1-yl]propyl]tetrahydro-4-hydroxy-2H-pyran-2-one.

Compounds of the present invention where $R_2$ and $R_3$ are hydrogen are prepared by the methods outlined in Reaction Sequence 1 or Reaction Sequence 2. As shown in Reaction Sequence 1, the aldehydes, VI, are reacted with the appropriately substituted vinylketones, VII, in the presence of the thiazolium salt, VIII, and a base such as triethylamine, to produce the diketones, IX. (See *Ang. Chem. Int. Ed.*, 15: 639–712 (1976)).

The diketones, IX, are reacted with an omega-aminoalkylnitrile (compound Roman numeral ten where the value of X is methylene, ethylene, or 1-methylethylene) in acetic acid to produce the disubstituted pyrrole nitriles, XI.

Treatment of the pyrrole nitriles, XI, with diisobutylaluminum hydride in an inert solvent such as dichloromethane produces the corresponding pyrrole aldehydes, XII.

in a polar solvent such as tetrahydrofuran, through which a small quantity of air has been bubbled. A slight excess of a trialkylborane, such as tributylborane, is added to the mixture which is then cooled to a temperature of preferably between about 0° C. and −78° C. after which sodium borohydride is added.

After stirring this mixture for about one to two hours, the mixture is oxidized with basic hydrogen peroxide. The reaction produces the 7-(substituted-pyrrolyl)-3,5-dihydroxyheptanoic acids, XIV, in which the product contains a predominance of the desired R*, R* configuration at carbon atoms three and five which bear the hydroxy groups.

The acids may be converted to a corresponding pharmaceutically acceptable salt by conventional methods or, alternatively, cyclized to the 6-[2-(substituted-pyrrol-1-yl)alkyl]pyran-2-ones, I, by dehydration in an inert solvent such as refluxing toluene with azeotropic removal of water. This cyclization reaction is found to produce material containing from 85–90% of the desired active trans-configuration of the 4-hydroxy group relative to the 6-(substitutedpyrrolyl)alkyl group on the pyran-2-one lactone ring.

REACTION SEQUENCE 1

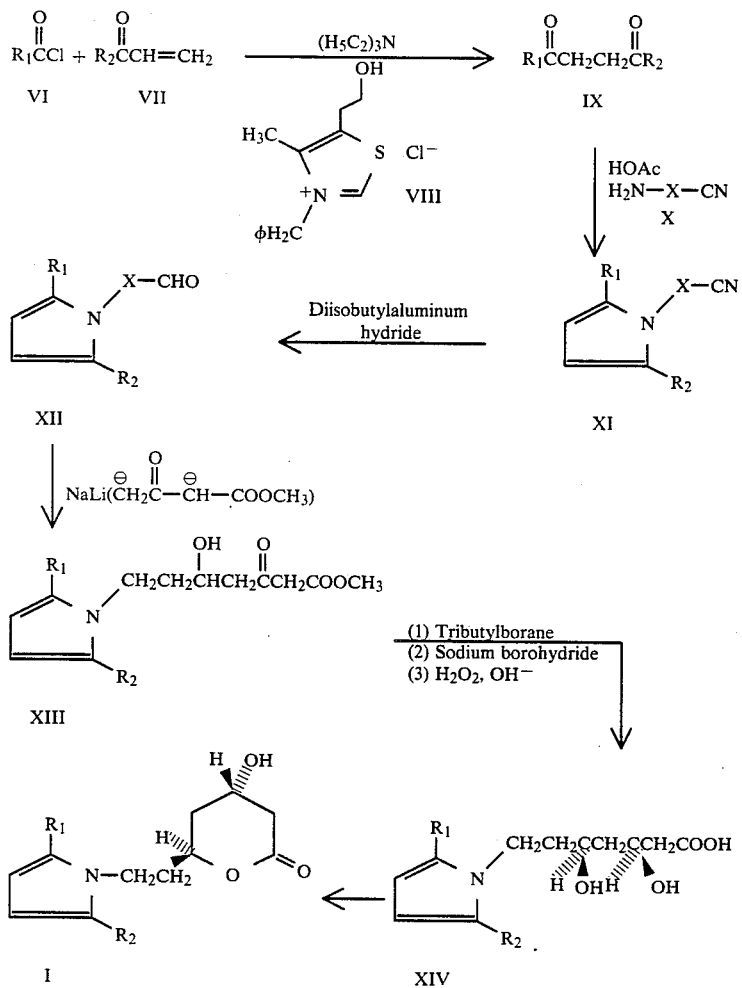

Reaction of the pyrrole aldehydes, XII, with the dilithium or lithium sodium salt methyl acetoacetate produces the 7-(substitutedpyrrolyl)-5-hydroxy-3-oxoheptanoates, XIII. The heptanoates, XIII, are dissolved Alternative procedures for preparing compounds of formula I of this invention where $R_2$ and $R_3$ are hydrogen, and for preparing intermediates, are illustrated in Reaction Sequence 2. As shown in Reaction Sequence 2, the diketones, IX, can be prepared by reacting the known alpha-haloketones, XV, with the sodium salt of known beta-ketoesters, XVI, followed by hydrolysis and decarboxylation in the conventional manner. The diketones, IX, are reacted with ammonium acetate in acetic acid to produce the cyclized 2,5-disubstituted pyrroles, XVII.

REACTION SEQUENCE 2

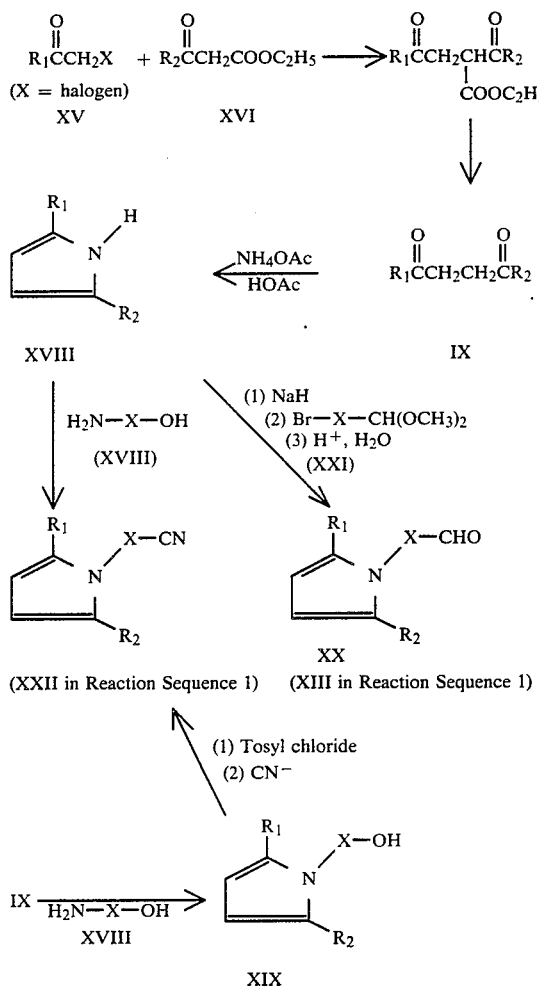

An alternative for this step, preferred when $R_1$ and/or $R_4$ are sterically bulky groups, involves reaction of the diketones, IX, with an omega-hydroxyalkyl amine (compound XVIII where X is methylene, ethylene, 1-methylethylene), to produce the N-(omega-hydroxyalkyl)-2,5-disubstitutedpyrroles, XIX.

The 2,5-disubstitutedpyrroles, XVII, are converted to the omega-(substitutedpyrrolyl)aldehydes, XX, by sequential reaction with sodium hydride, a 1,1-dimethoxy-omega-bromoalkane (compound XXI where X is methylene, ethylene, 1-methylethylene, or vinyl), and then acid. The aldehydes, XX, are subsequently used in the preparation of compounds of formula I of this invention as illustrated above in Reaction Sequence 1.

The 2,5-disubstituted pyrroles, XVII, are converted to the corresponding (2,5-disubstitutedpyrrolyl)nitriles, XXII (when X is ethylene), by reaction with acrylonitrile or, alternatively (when X is other than ethylene), by starting with compounds of formula XIX. In this latter instance, the hydroxy functionality of compounds of formula XIX is converted to the p-toluenesulfonate by conventional means, and the tosylate group is subsequently displaced by cyanide ion to produce the nitriles of formula XXII. The compounds of formula XXII are subsequently used in the preparation of compounds of formula I of this invention by methods detailed in Reaction Sequence 1 above.

Starting materials and intermediates employed in Reaction Sequences 1 and 2 above may be prepared by the general methods outlined in Reaction Sequence 3. For example, as shown there, the vinyl ketones, XII, are prepared by either of the two methods illustrated. In one method, the known acid chlorides, XXIII, are reacted with the trimethylsilylethene, XXIV, in the presence of anhydrous aluminum chloride in dichloromethane.

In the alternative method of preparing the vinyl ketones, VII, which is preferred when $R_1$ is an aromatic substituent such as phenyl or substituted phenyl, the

REACTION SEQUENCE 3

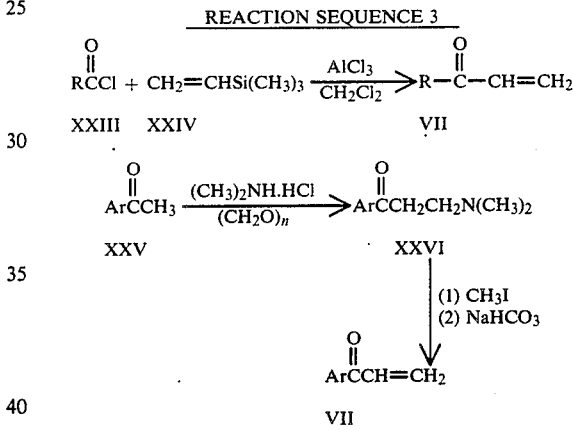

known methyl aryl ketones, XXV, are converted to (dimethylaminoethyl)aryl ketones, XXVI, and then by deamination to the vinyl ketones, VII.

The compounds of the present invention of formula I where the groups $R_2$ and $R_3$ are other than hydrogen or halogen can be synthesized by the methods detailed in Reaction Sequences 4–8.

Employing the method detailed in Reaction Sequence 4 the compounds of the present invention where $R_2$ and $R_3$ are both halogen can be prepared by the halogenation of the unsubstituted compounds with N-halosuccinimide in a three-step process involving the prior protection of the 4-hydroxy group of the lactone ring. Thus, for example, the 2,5-disubstitutedpyrrol-1-yl compounds, XXVII, are first converted to the corresponding tert-butyl-dimethylsilyl ethers, XXVIII. The protected compounds and then chlorinated with N-chlorosuccinimide in a polar solvent such as dimethylformamide to produce the silylated 3,4-dichloro compounds, XXIX. The protecting silyl ether group is subsequently removed by reaction with a buffered fluoride reagent such as tetrabutylammonium fluoride in a mixed acetic acid/tetrahydrofuran solvent system to produce the dichloro compounds, XXX.

Alternatively, as detailed in Reaction Sequence 5, the (2,5-disubstitutedpyrrol-1-yl)alkyl nitriles, XI (see Reaction Sequence 1) are halogenated by employing an N-halosuccinimide in dimethylformamide to provide the 2,5-disubstituted-3,4-dihalopyrroles, XXXI. (See Aiello, et al., *J. Het. Chem.*, 19: 977 (1982)). These compounds can then be subsequently converted to the compounds of the present invention by conventional methods detailed in Reaction Sequence 1.

A third method takes advantage of the chemistry of mesionic compounds of the type described originally by R. Huisgen, et al., *Ang. Chem. Int. Ed.*, 3: 136 (1964). In this procedure, detailed in Reaction Sequence 6, an N-alkyl-N-acylamino acid is treated with an acid anhydride and a substituted acetylenic compound to produce a pyrrole. For example, Reaction Sequence 6 shows how reaction of an alpha-halo ester, XXXII, with 2-(1-(2-aminoethyl))-1,3-dioxalane in triethylamine provides the N-alkyl-alpha-aminoester, XXXIII. The aminoester, XXXIII is acylated with an acid chloride and subsequently hydrolyzed in base to produce the N-acyl-N-alkyl aminoacid, XXXIV. Reaction of this latter compound with the desired substituted acetylenic compound, XXXV, produces the substituted pyrrole compounds, XXXVI. Acidic hydrolysis of XXXVI yields the aldehyde compounds, XXXVII, analogous to compounds XII of Reaction Sequence 1. Compounds of formula XXXVII are used in subsequent steps in a manner detailed in Reaction Sequence 1 to produce compounds of the present invention.

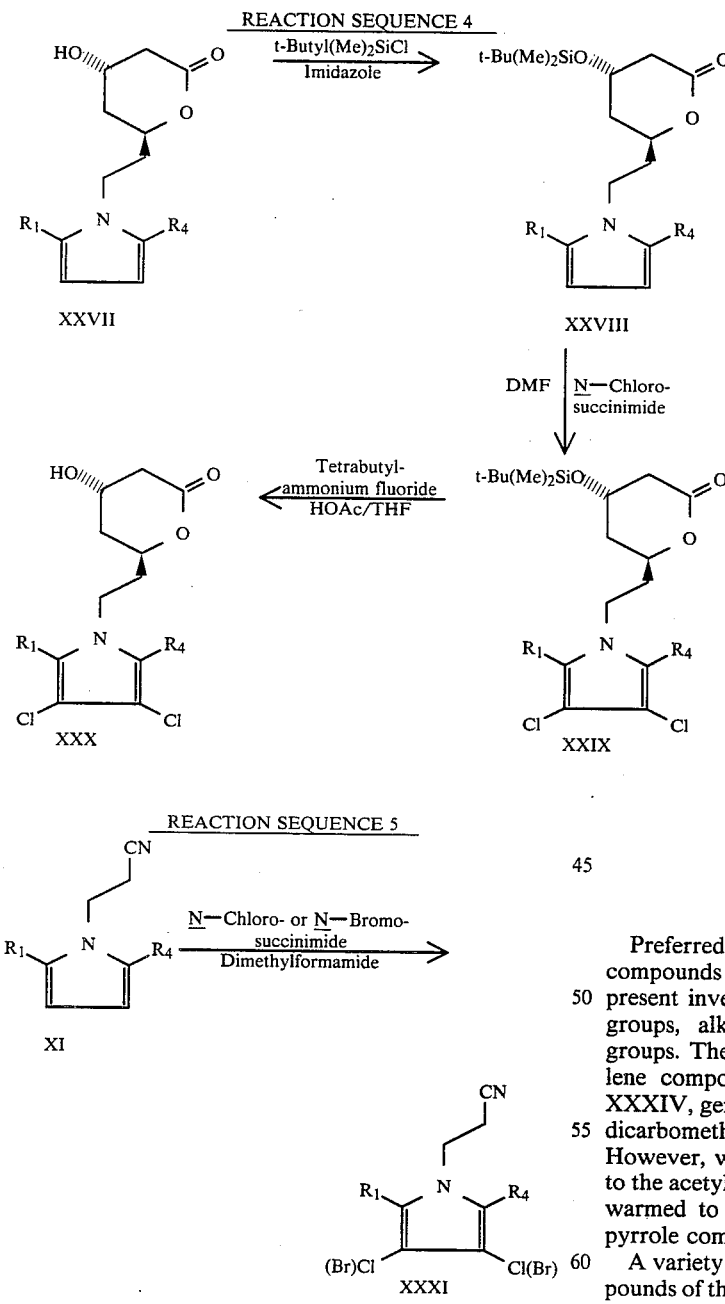

Preferred substituents for the substituted acetylenic compounds in this method of making compounds of the present invention include carboalkoxy groups, phenyl groups, alkanoyl groups, alkyl groups and cyano groups. The reaction between the disubstituted acetylene compound and the N-acyl-N-alkyl aminoacids, XXXIV, generally proceeds smoothly; for example, the dicarbomethoxy acetylene reacts smoothly at 25° C. However, when only one activating group is attached to the acetylene, the reaction mixture must generally be warmed to 70°–110° C. to obtain high yields of the pyrrole compounds.

A variety of other pyrroles can be derived from compounds of the general formula XXXVI when the groups $R_2$ and $R_3$ are carbomethoxy. Some of these transformations are detailed in Reaction Sequences 7 and 8. For example, as shown in Reaction Sequence 7, reduction of XXXVI with a reducing agent such as lithium aluminum hydride results in the bis(hydroxymethyl)pyrrole which can be subsequently further reduced to the dimethyl compound,

REACTION SEQUENCE 6

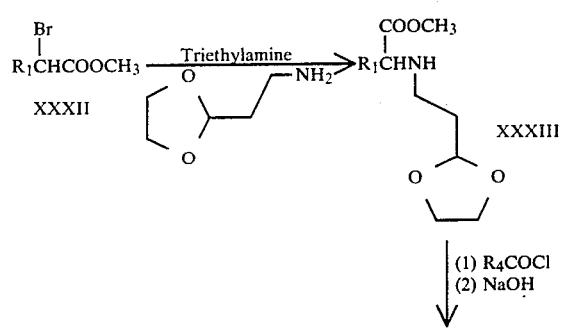

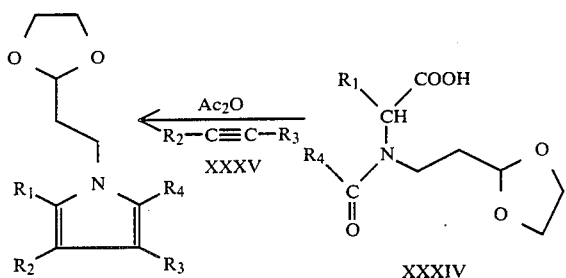

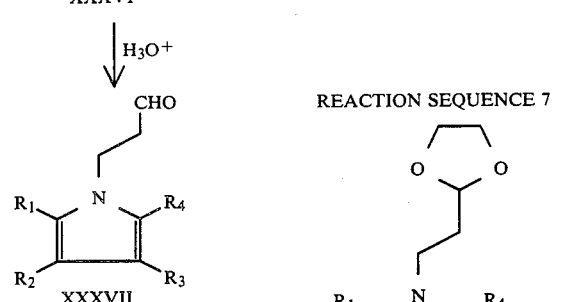

REACTION SEQUENCE 7

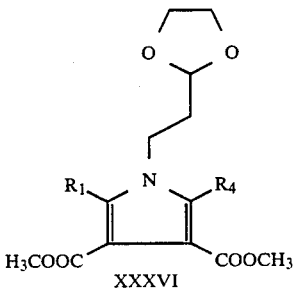

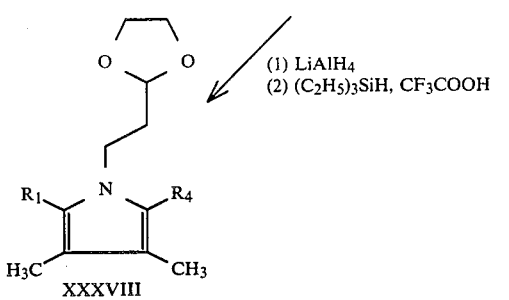

XXXVIII, by means of triethylsilane and trifluoroacetic acid employing the procedure of West, et al., *J. Org. Chem.*, 38: 2675 (1973)).

Alternatively, as shown in Reaction Sequence 8, reaction of the compounds of formula XXXVI with a Grignard reagent or an alkyl-lithium reagent in the conventional manner followed by reduction and standard work-up affords the higher dialkylpyrroles, XXXIX.

Reaction of the diesters, XXXVI, or the corresponding diacids (obtained by conventional hydrolysis) with secondary amines provides the bis(dialkylamides), XL.

Alternatively, reaction of XXXVI with primary amines, followed by thermal cyclization in the conventional manner, provides the pyrrolosuccinimides, XLI, which can be reduced to XLII, if desired by reducing agents such as lithium aluminum hydride.

The bis(hydroxymethyl)pyrrole compounds derived from the lithium aluminum hydride reduction of XXXVI can be converted to their corresponding esters or carbamates by reaction with the desired acid anhydride or isocyanate, respectively. (See Anderson, et al., *J. Med. Chem.*, 22: 977 (1979)).

The acids, XLIII, derived by convention hydrolysis of compounds of formula XXXVI can also be converted to the bis(amido)pyrroles, XLIV, which in turn can be dehydrated to produce the bis(nitrilo)pyrroles, XLV. Lastly, if desired, the bis(alkanoyl)pyrroles, XLVI, can be derived from the bis(nitrilo)pyrroles by reaction in the convention manner with the appropriate Grignard reagents.

The ring-opened dihydroxy-acids of structural formula II above are intermediates in the synthesis of the lactone compounds in accordance with the above-detailed reaction methods, or may be produced from the lactone compounds by conventional hydrolysis of the lactone compounds of formula I.

REACTION SEQUENCE 8

(Throughout this sequence, A = —CH$_2$CH$_2$—⟨dioxolane⟩)

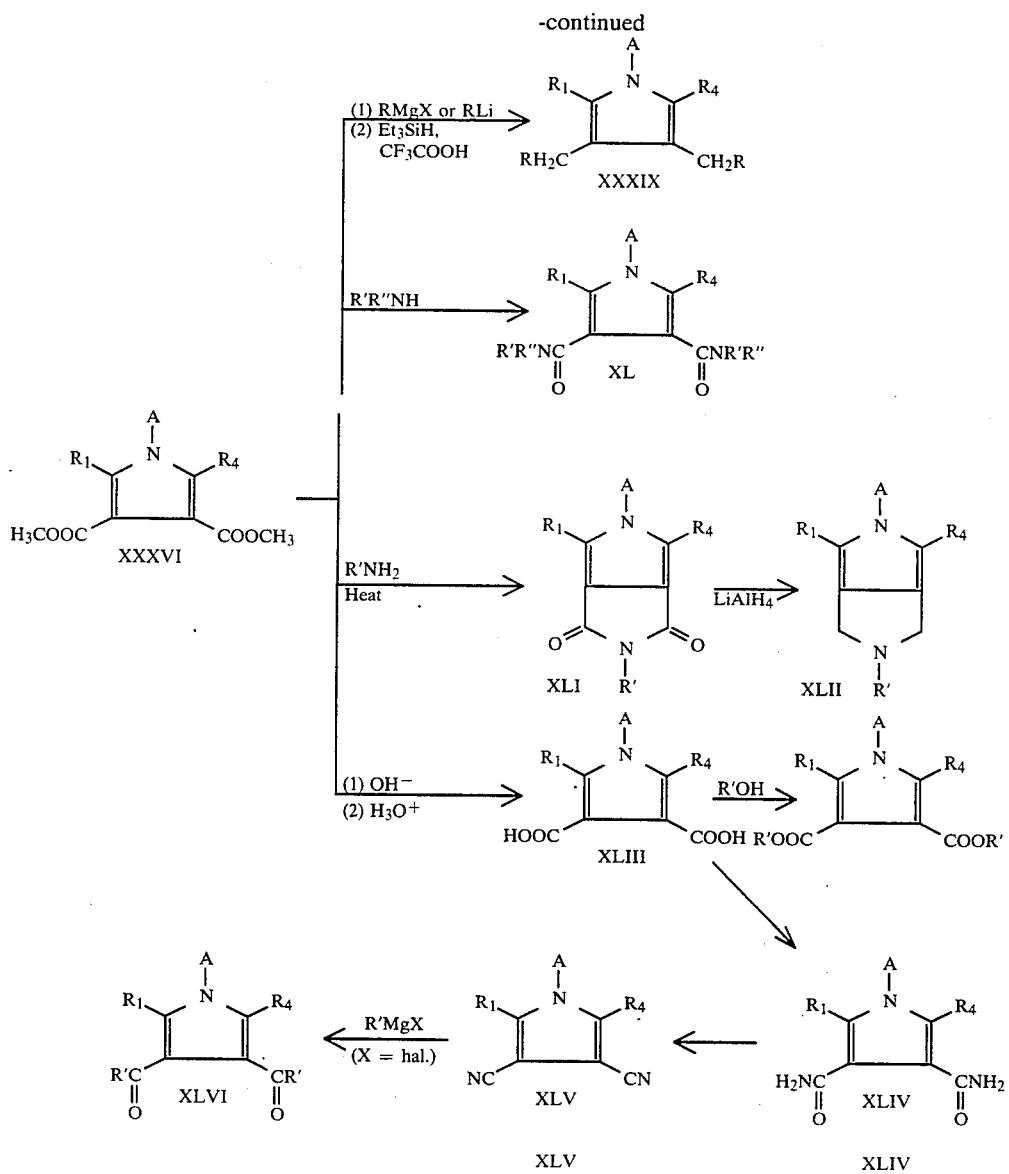

In the ring-opened dihydroxy acid form, compounds of the present invention react to form salts with pharmaceutically acceptable metal and amine cations formed from organic and inorganic bases.

The term "pharmaceutically acceptable metal cation" contemplates positively charged metal ions derived from sodium, potassium, calcium, magnesium, aluminum, iron, zinc and the like.

The term "pharmaceutically acceptable amine cation" contemplates the positively charged ions derived from ammonia and organic nitrogenous bases strong enough to form such cations. Bases useful for the formation of pharmaceutically acceptable nontoxic base addition salts of compounds of the present invention form a class whose limits are readily understood by those skilled in the art.

The free acid form of the compound may be regenerated from the salt, if desired, by contacting the salt with a dilute aqueous solution of an acid such as hydrochloric acid.

The base addition salts may differ from the free acid form of compounds of this invention in such physical characteristics as melting point and solubility in polar solvents, but are considered equivalent to the free acid forms for purposes of this invention.

The compounds of this invention can exist in unsolvated as well as solvated forms. In general, the solvated forms, with pharmaceutically acceptable solvents such as water, ethanol, and the like, are equivalent to the unsolvated forms for purposes of this invention.

The compounds of this invention are useful as hypocholesterolemic or hypolipidemic agents by virtue of their ability to inhibit the biosynthesis of cholesterol through inhibition of the enzyme 3-hydroxy-3-methyl-glutaryl-coenzyme A reductase (HMG-CoA reductase).

The ability of compounds of the present invention to inhibit the biosynthesis of cholesterol was measured by two methods. A first method (designated CSI screen) utilized the procedure described by R. E. Dugan et al., *Archiv. Biochem. Biophys.*, (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of cholesterol-$^{14}$C-acetate into nonsaponifiable lipid by the rat liver homogenate is measured. The micromolar concentration of compound required for 50% inhibition of sterol synthesis over a one-hour period is measured, and expressed as an IC$_{50}$ value.

A second method (designated COR screen) employed the procedure detailed by T. Kita, et al., *J. Clin. Invest.*, (1980), 66: 1094–1100. In this method, the amount of $^{14}$C-HMG-CoA converted to $^{14}$C-mevalonate in the presence of a purified enzyme preparation of HMG-CoA reductase was measured. The micromolar concentration of compound required for 50% inhibition of cholesterol synthesis was measured and recorded as an IC$_{50}$ value.

The activity of several representative examples of compounds in accordance with the present invention appears in Table 1, and is compared with that of the prior art compound, compactin. In particular, compounds of the present invention where R$_2$ and R$_3$ are substituents other than hydrogen have activities comparable to that of the natural product, compactin.

sugar, lactose, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as carrier providing a capsule in which the active component (with or without other carriers) is surrounded by a carrier, which is thus in accordance with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions for oral use can be prepared by dissolving the active component in water and adding suitable colorants, flavoring agents, stabilizers, and thickening agents as desired. Aqueous suspensions for oral use can be made by dispersing the finely divided active component in water with viscous material, i.e., natural or synthetic gums, resins, methyl, cellulose, sodium carboxymethyl cellulose, and other well-known suspending agents.

TABLE 1

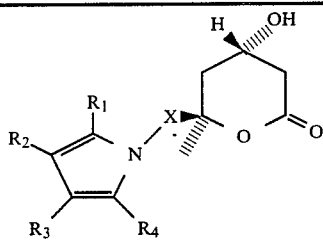

| Compound | X | R$_1$ | R$_2$ | R$_3$ | R$_4$ | IC$_{50}$ (Micromoles/Liter) CSI | COR |
|---|---|---|---|---|---|---|---|
| 1 | —CH$_2$CH$_2$— | 4-Fluorophenyl | H | H | —CH(CH$_3$)$_2$ | 0.48 | 0.28 |
| 2 | —CH$_2$CH$_2$— | 4-Fluorophenyl | Cl | Cl | —CH(CH$_3$)$_2$ | 0.16 | 0.024 |
| 3 | —CH$_2$CH$_2$— | 4-Fluorophenyl | Br | Br | —CH(CH$_3$)$_2$ | 0.22 | 0.001 |
| 4 | —CH$_2$CH$_2$— | 4-Fluorophenyl | —COOCH$_3$ | —COOCH$_3$ | —CH(CH$_3$)$_2$ | 0.11 | 0.080 |
| 5 | Compactin (prior art) | | | | | 0.026 | 0.028 |

*Adjusted for a standard IC$_{50}$ value for compactin which was used as an internal standard in the test.

For preparing pharmaceutical compositions from the compounds described by this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with finely divided active compound. In tablets, the active compound is mixed with the carrier having the necessary binding properties in suitable proportions and compacted in the shape and size desired.

For preparing suppository preparations, a low-melting wax such as a mixture of fatty-acid glycerides and cocoa butter is first melted, and the active ingredient is dispersed homogeneously therein, as by stirring. The molten homogeneous mixture is then poured into convenient sized molds and allowed to cool and solidify.

The powders and tablets preferably contain 5 to about 70% of the active ingredient. Suitable solid carriers are magnesium carbonate, magnesium stearate, talc, Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these packaged forms.

In therapeutic use as hypolipidemic or hypocholesterolemic agents, the compounds utilized in the pharmaceutical method of this invention are administered to the patient at dosage levels of from 40 mg to 600 mg per day. For a normal human adult of approximately 70 kg or body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of trans-6-[2-[2-(4-fluorophenyl)-5-(1-methylethyl)-1H-pyrrol-1-yl]ethyl]tetrahydro-4-hydroxy-2H-pyran-2-one Step A: Preparation of 1-(4-fluorophenyl)-5-methyl-1,4-hexanedione.

A mixture of 1-(4-fluorophenyl)-2-propene-1-one (43 g, 286.7 mmol) prepared in accordance with the method detailed in Org. Syn., Coll. Vol. IV, 305, was mixed with 31.2 ml (344 mmol) of isobutraldehyde, 28 ml (200 mmol) of triethylamine, and 14.5 g (57.7 mmol) of 2-(2-hydroxyethyl)-3-methyl-4-benzylthiazolium chloride and the mixture stirred under nitrogen at 70° C. for 12 hours.

After this time, the mixture was cooled to room temperature and the cooled mixture was partitioned between ether (500 ml) and water (100 ml). The aqueous layer was further extracted with 300 ml of ether, the ether solutions combined and washed successively with 200 ml of water, two 200-ml portions of 2M hydrochloric acid, and 100 ml of brine, and finally dried over anhydrous magnesium sulfate.

The ether was removed, and the residue was distilled (bp 115°-120° C., 0.2 mm Hg) to provide 36.7 g (165 mmol, 58% of 1-(4-fluorophenyl)-5-methyl-1,4-hexanedione which solidified upon standing.

Alternate Step A: Preparation of 1-(4-fluorophenyl)-5-methyl-1,4-hexanedione.

Isopropyl vinyl ketone (1.97 g, 20 mmol), prepared from isobutyryl chloride and vinyl trimethylsilane in accordance with the method detailed in *Tet. Letters*, (1979), 1995, was mixed with 4-fluorobenzaldehyde (2.4 g, 20 mmol), 2 ml (14 mmol) of triethylamine, and 1.0 g (4.0 mmol) of 2-(2-hydroxyethyl)-3-methyl-4-benzylthiazolium chloride. The mixture was stirred and heated under nitrogen for five hours. After cooling to room temperature, the mixture was partitioned between ether (200 ml) and water (50 ml). The water layer was extracted with 200 ml of ether and the ether solutions were combined. The combined ether solution was washed successively with 50 ml of water, two 50-ml portions of 2M hydrochloric acid, and 50 ml of brine. The ether solution was dried over anhydrous magnesium sulfate. After removal of the ether, the remaining liquid was flash chromatographed on silica gel eluting with 20:1 (volume/volume) hexane-ethyl acetate. This procedure afforded 2.59 g of pure 1-(4-fluorophenyl)-5-methyl-1,4-hexanedione, mp 47°-49° C.

Step B: Preparation of 2-[2-[2-(4-fluorophenyl)-5-(1-methylethyl)-5-methyl-1H-pyrrol-1-yl]]-1-cyanoethane.

A solution of 1-(4-fluorophenyl)-5-methyl-1,4-hexanedione (36.5 g, 164 mmol), 3-aminopripionitrile.½ fumarate (23.1 g, 180.4 mmol), and p-toluenesulfonic acid (0.1 g) in 250 ml of glacial acetic acid was stirred and heated under reflux under nitrogen for six hours. After cooling to room temperature, the mixture was poured into 500 ml of ice-water and the water suspension which resulted was extracted with two 600-ml portions of ether. The combined ether extract was washed successively with rwo 200-ml portions of water, three 200-ml portions of sodium bicarbonate, and a 200-ml portion of brine and then dried over anhydrous magnesium sulfate.

The ether was removed, and the liquid which remained was flash chromatographed on silica gel, eluting with 10:1 (volume/volume) hexane-ethyl acetate to yield 34.8 g of oily 2-[2-[2-(4-fluorophenyl)-5-(1-methylethyl)-1H-pyrrol-1-yl]]-1-cyanoethane which solidified upon standing.

Recrystallization from isopropyl ether provided analytical material of melting point 78°-80° C.

Anal. Calcd. for $C_{16}H_{17}FN_2$: C, 74.97%; H, 6.69%; N, 10.93%. Found: C, 75.18%; H, 6.64%; N, 10.93%.

Step C: Preparation of 3-[2-[2-(4-fluorophenyl)-5-(1-methylethyl)-1H-pyrrol-1-yl]]-1-propanal.

To a stirred solution of 2-[2-[2-(4-fluorophenyl)-5-(1-methylethyl)-1H-pyrrol-1-yl]]-1-cyanoethane (34.8 g, 135.8 mmol) in 300 ml of dichloromethane at ambient temperature under nitrogen was added dropwise over 30 minutes 156.2 ml of a 1.0M solution of diisobutyl-aluminum ("DiBAL") in dichloromethane. The resulting mixture was stirred for three hours, after which another 20 ml of 1.0M DiBAL solution was added. The mixture was stirred overnight at room temperature, after which the excess hydrode was destroyed by cautious addition of methanol. When gas evolution had ceased, the solution was carefully poured into 500 ml of vigorously stirred ice-cold 2M hydrochloric acid.

The emulsion which resulted was extracted with two 500-ml portions of ether and the combined ether extracts were washed successively with 100 ml of water, two 100-ml portions of sodium bicarbonate solution, and 100 ml of brine, and then dried over anhydrous magnesium sulfate. The ether was removed and the residue was flash chromatographed over silica gel, eluting with 10:1 (volume/volume) hexane-ethyl acetate, yielding pure 3-[2-[2-(4-fluorophenyl)-5-(1-methylethyl)-1H-pyrrol-1-yl]]-1-propanal.

Step D: Preparation of methyl 7-[2-[2-(4-fluorophenyl)-5-(1-methylethyl)-1H-pyrrol-1-yl]]-5-hydroxy-3-oxo-heptanoate.

To a stirred suspension of 2.17 g (90.6 mmol) of hex-ane-washed sodium hydride in 200 ml of anhydrous tetrahydrofuran, cooled to 0° C. under nitrogen, was added dropwise over a period of 30 minutes a solution of 8.9 ml (82.4 mmol) of methyl acetoacetate in 150 ml of anhydrous tetrahydrofuran. When gas evolution had ceased, 39.3 ml of a 2.1M solution of n-butyl lithium in hexane was added dropwise. The resulting solution was stirred for 30 minutes after which a solution of 19.4 g (74.9 mmol) of 3-[2-[2-(4-fluorophenyl)-5-(1-methylethyl)-1H-pyrrol-1-yl]]-1-propanol in 150 ml of anhydrous tetrahydrofuran was added dropwise over a period of 30 minutes. The solution was stirred for an additional hour before quenching the reaction by the addition of 100 ml of saturated aqueous ammonium chloride solution, followed by 100 ml of 2M hydrochloric acid solution.

The resulting mixture was partitioned between ether (500 ml) and water (100 ml). The water layer was separated and extracted with 300 ml of ether. The ether extracts were combined and washed with 50 ml of brine and then dried over anhydrous magnesium sulfate. The ether was removed and the residue was flash chromatographed on silica gel, eluting with 5:1 (volume/volume) hexane-ethyl acetate to yield 19.9 g (64%) of methyl 7-[2-[2-(4-fluorophenyl)--

-5-(1-methylethyl)-1H-pyrrol-1-yl]]-5-hydroxy-3-oxoheptanoate.

Step E: Preparation of trans-6-[2-[2-(4-fluorophenyl)-5-(1-methylethyl)-1H-pyrrol-1-yl]ethyl]tetrahydro-4-hydroxy-2H-pyran-2-one.

Thirty ml of air (syringe) were bubbled through a solution of 58 ml of a 1M solution of tributylborane in tetrahydrofuran containing 19.9 g (53 mmol) of methyl 7-[2-[2-(4-fluorophenyl)--5-(1-methylethyl)-1H-pyrrol-1-yl]]-5-hydroxy-3-oxoheptanoate under nitrogen at room temperature. The solution was then stirred for 18 hours at room temperature and then cooled to $-78°$ C. Sodium borohydride (2.27 g, 60 mmol) was then added in one portion. The mixture was stirred for 60 minutes at $-78°$ C. and for 90 minutes at $0°$ C. A mixture of 10 ml water and 10 ml of methanol was carefully added (gas evolution). Sixty ml of 3M sodium hydroxide solution and 30 ml of 30% $H_2O_2$ solution were simultaneously added to the mixture from separation dropping funnels. The vigorously stirred mixture was held at $0°$ C. for 60 minutes and then at room temperature for two hours.

The mixture was then partitioned between 300 ml of water and 300 ml of ether. The ether layer was extracted with 50 ml of 10% sodium hydroxide solution and the water layers were combined, acidified with concentrated hydrochloric acid, and extracted with two 500-ml portions of ethyl acetate. The ethyl acetate extracts were combined, washed twice with brine, and dried over anhydrous magnesium sulfate. Removal of the ethyl acetate yielded 12.5 g of an oily acid which was dissolved in 500 ml of toluene and heated to azeotropically remove water. After cooling the solution to room temperature and removing the toluene, the residue was flash chromatographed on silica gel, eluting with 2:1 hexane-ethyl acetate (volume/volume) to yield 11 g of a colorless solid. Recrystallization from diisopropyl ether yielded 9.5 g (52%) of trans-6-[2-[2-(4-fluorophenyl-5-(1-methylethyl)-1H-pyrrol-1-yl]tetrahydro-4-hydroxy-2H-pyran-2-one, mp 104°–105° C.

Anal. Calcd. for $C_{20}H_{24}FNO_3$: C, 70.42; H, 7.00; N, 4.06; Found: C, 70.26; H, 7.33; N, 3.99.

EXAMPLE 2

Preparation of trans-6-[2-[2-(4-fluorophenyl)-5-methyl-1H-pyrrol-1-yl]ethyl]tetrahydro-4-hydroxy-2H-pyran-2-one The procedure of Example 1 was employed with the substitution of equimolar amounts of 4-fluorobenzaldehyde and 3-butene-2-one for the 1-(4-fluorophenyl)-2-propene-1-one and isobutyraldehyde in Step A of Example 1. Thereafter, the procedure of Steps B-E were followed to produce trans-6-[2-[2-(4-fluorophenyl)-5-methyl-1H-pyrrol-1-yl]ethyl]tetrahydro-4-hydroxy-2H-pyran-2-one.

Anal. Calcd. for $C_{18}H_{20}FNO_3$: C, 68.12; H, 6.35; N, 4.41; Found: C, 68.39; H, 6.18; N, 4.25.

EXAMPLE 3

Preparation of trans-6-[2-2-cyclopropyl-5-(4-fluorophenyl)-1H-pyrrol-1-yl]ethyl]tetrahydro-4-hydroxy-2H-pyran-2-one The procedure of Example 1 was employed with the substitution of equimolar amounts of 4-fluorobenzaldehyde and 1-cyclopropyl-2-propene-1-one for the 1-(4-fluorophenyl)-2-propene-1-one and isobutyraldehyde in Step A of Example 1. Thereafter, the procedure of Steps B-E were followed to produce trans-6-[2-[2-cyclopropyl-5-(4-fluorophenyl)-1H-pyrrol-1-yl]ethyl]-tetrahydro-4-hydroxy-2H-pyran-2-one.

Anal. Calcd. for $C_{20}H_{22}FNO_3$: C, 69.69; H, 6.46; N, 4.08; Found: C, 70.02; H, 6.54; N, 4.01.

EXAMPLE 4

Preparation of trans-6-[2-[2-(1,1-dimethylethyl)-5-(4-fluorophenyl)-1H-pyrrol-1-yl]ethyl]tetrahydro-4-hydroxy-2H-pyran-2-one The procedure of Example 1 was employed with the substitution of equimolar amounts of 4-fluorobenzaldehyde and t-butyl vinyl ketone for the 1-(4-fluorophenyl)-2-propene-1-one and isobutyraldehyde in Step A of Example 1. Thereafter, the procedure of Steps B-E were followed to produce trans-6-[2-[2-(1,1-dimethylethyl)-5-(4-fluorophenyl)-1H-pyrrol-1-yl]ethyl]tetrahydro-4-hydroxy-2H-pyran-2-one, mp 177°–178° C.

Anal. Calcd. for $C_{21}H_{26}FNO_3$: C, 70.17; H, 7.29; N, 3.90; Found: C, 70.22; H, 7.50; N, 3.80.

Example 5

Preparation of trans-6-[2-(5-phenyl-2-methyl)-1H-pyrrol-1-yl]ethyl]-tetrahydro-4-hydroxy-2H-pyran-2-one The procedure of Example 1 was employed with the substitution of equimolar amounts of benzaldehyde and 3-butene-2-one for the 1-(4-fluorophenyl)-2-propene-1-one and isobutyraldehyde in Step A of Example 1. Thereafter, the procedure of Steps B-E were followed to produce trans-6-[2-(5-phenyl-2-methyl)-1H-pyrrol-1-yl]ethyl]tetrahydro-4-hydroxy-2H-pyran2-one, mp 95°–96° C.

Anal. Calcd. for $C_{19}H_{23}NO_4$: C, 69.28; H, 7.04; N, 4.25; Found: C, 68.93; H, 7.00; N, 4.10.

EXAMPLE 6

Preparation of trans-tetrahydro-4-hydroxy-6-[2-[2-(2-methoxyphenyl)-5-methyl-1H-pyrrol-1-yl]ethyl]-2H-pyran-2-one The procedure of Example 1 was employed with the substitution of equimolar amounts of 2-methoxybenzaldehyde and methyl vinyl ketone for the 4-(fluorobenzaldehyde and isopropyl vinyl ketone in Alternate Step A of Example 1. Thereafter, the procedure of Steps B-E were followed to produce trans-tetrahydro-4-hydroxy-6-[2-[2-(2-methoxyphenyl)-5-methyl-1H-pyrrol-1-yl]ethyl]-2H-pyran-2-one, mp 112.5°–113.5° C.

Anal. Calcd. for $C_{19}dH_{23}NO_4$: C, 69.28; H, 7.04; N, 4.25; Found: C, 69.04; H, 7.22; N, 4.17.

EXAMPLE 17

Preparation of trans-tetrahydro-4-hydroxy-6-[2-[2-(4-methoxyphenyl)-5-methyl-1H-pyrrol-1-yl]ethyl]-2H-pyran-2-one The procedure of Example 1 was employed with the substitution of equimolar amounts of 4-methoxybenzaldehyde and 3-butene-2-one for the 1-(4-fluorophenyl)-2-propene-1-one and isobutyraldehyde in Step A of Example 1. Therafter, the procedure of Steps B-E were followed to produce trans-tetrahydro-4-hydroxy-6-[2-[2-(4-methoxyphenyl)-5-methyl-1H-pyrrol-1-yl]ethyl]-2H-pyran-2-one, mp 95°–95° C.

Anal. Calcd. for C₁₉H₂₃NO₄:C, 69.28; H, 7.04; N, 4.25; Found: C, 68.93; H, 7.00; N, 4.10.

EXAMPLE 8

Preparation of trans-6-[2-(2-cyclohexyl-5-methyl-1H-pyrrol-1-yl)ethyl]tetrahydro-4-hydroxy-2H-pyran-2-one The procedure of Example 1 was employed with the substitution of equimolar amounts of cyclohexanecarboxaldehyde and 3-butene-2-one for the 1-(4-fluorophenyl)-2-propene-1-one and isobutyraldehye in Step A of Example 1. Thereafter, the procedure of Steps B–E were followed to produce trans-6-[2-(2-cyclohexyl-5-methyl-1H-pyrrol-1-yl)ethyl]tetrahydro-4-hydroxy-2H-pyran-2-one, mp 129°–130° C.

Anal. Calcd. for $C_{18}H_{27}NO_3$: C, 70.79; H, 8.91; N, 4.59; Found: C, 71.11; H, 8.71; N, 4.47.

EXAMPLE 9

Preparation of trans-tetrahydro-4-hydroxy-6-[2-[2-methyl-5-[3-(trifluoromethyl)phenyl]-1H-pyrrol-1-yl]ethyl]-2H-pyran-2-one The procedure of Example 1 was employed with the substitution of equimolar amounts of 3-(trifluoromethyl)benzaldehyde and 3-butene-2-one for the 1-(4-fluorophenyl)-2-propene-1-one ad isobutyraldehyde in Step A of Example 1. Thereafter, the procedure of Steps B–E were followed to produce trans-tetrahydro-4-hydroxy-6-[2-[2-methyl-5-[3-(trifluoromethyl)phenyl]-1H-pyrrol-1yl]ethyl]-2H-pyran-2-one.

Anal. Calcd. for $C_{19}H_{20}F_3NO_3$: C, 62.12; H, 5.49; N, 3.81; Found: C, 62.22; H, 5.61; N, 3.73.

EXAMPLE 10

Preparation of trans-6-[2-[2-([1,1'-biphenyl]-4-yl)-5-methyl-1H-pyrrol-1-yl]ethyl]tetrahydro-4-hydroxy-2H-pyran-2-one The procedure of Example 1 was employed with the substitution of equimolar amounts of 4-phenylbenzaldehyde and 3-butene-2-one for the 1-(4-fluorophenyl)-2-propane-1-one and isobutyraldehyde in Step A of Example 1. Thereafter, the procedure of Steps B–E were followed to produce trans-6-[2-[2-([1,1'-biphenyl]-4-yl)-5-methyl-1H-pyrrol-1-yl]ethyl]tetrahydro-4-hydroxy-2H-pyran-2-one, mp 104°–107° C.

Anal. Calcd. for $C_{24}H_{25}NO_3$: C, 76.77; H, 6.71; N, 3.73; Found: C, 76.66; H, 6.66; N, 3.71.

EXAMPLE 11

Preparation of trans-tetrahydro-4-hydroxy-6-[2-[2-methyl-5-(1-naphthalenyl)-1H-pyrrol-1-yl]-2H-pyran-2-one The procedure of Example 1 was employed with the substitution of equimolar of 1-naphthaldehyde and 3-butene-2-one for the 1-(4-fluorophenyl)-2-propene-1-one and isobutyraldehyde in Step A of Example 1. Thereafter, the procedure of Steps B–E were followed to produce trans-tetrahydro-4-hydroxy-6-[2-[2-methyl-5-(1-naphthalenyl)-1H-pyrrol-1-yl]ethyl]-2H-pyran-2-one, mp 137°–138° C.

EXAMPLE 12

Preparation of trans-tetrahydro-4-hydroxy-6-[2-[2-methyl-5-(2-naphthalenyl)-1H-pyrrol-1-yl]ethyl]-2H-pyran-2-one The procedure of Example 1 was employed with the substitution of equimolar amounts of 2-naphthaldehyde and 3-butene-2-one for the 1-(4-fluorophenyl)-2-propene-1-one and isobutyraldehyde in Step A of Example 1. Thereafter, the procedure of Steps B–E were followed to produce trans-tetrahydro-4-hydroxy-6-[2-[2-methyl-5-(2-naphthalenyl)-1H-pyrrol-1-yl]ethyl]-2H-pyran-2-one, mp 45°–50° C.

Anal. Calcd. for $C_{22}H_{23}NO_3$: C, 75.62; H, 6.63; N, 4.00; Found: C, 75.12; H, 6.88; N, 3.97.

EXAMPLE 13

Preparation of trans-6-[2-(bicyclo[2.2.1]hept-5-en-2-yl-5-methyl-1H-pyrrol-1-yl)ethyl]-tetrahydro-4-hydroxy-2H-pyran-2-one The procedure of Example 1 was employed with the substitution of equimolar amounts of bicyclo [2.2.1]hept-5-ene-2-carboxyaldehyde (mixture of diastereomers) and 3-butene-2-one for the 1-(4-fluorophenyl)-2-propene-1-one and isobutyraldehyde in Step A of Example 1. Therafter, the procedure of Steps B–E were followed to produce trans-6-[2-(2-bicyclo[2.2.1]hept-5-en-2-yl-5-methyl-1H-pyrrol-1-yl)ethyl]tetrahydro-4-hydroxy-2H-pyran-2-one as a 1:1 mixture of the ando- and exoisomers at the norbornene ring, mp 125°–126° C.

Anal. Calcd. for $C_{19}H_{25}NO_3$: C, 72.35; H, 7.99; N, 4.44; Found: C, 72.11; H, 8.02; N, 4.32.

EXAMPLE 14

Preparation of trans-6-[2-[2-(diphenylmethyl)-5-methyl-1H-pyrrol-1-yl]ethyl]tetrahydro-4-hydroxy-2H-pyran-2-one The procedure of Example 1 was employed with the substitution of equimolar amounts of diphenylacetaldehyde and 3-butene-2-one for the 1-(4-fluorophenyl)-2-propene-1-one and isobutyraldehyde in Step A of Example 1. Thereafter, the procedure of Steps B–E were followed to produce trans-6-[2-[2-diphenylmethyl)-5-methyl-1H-pyrrol-1-yl]ethyl]tetrahydro-4-hydroxy-2H-pyran-2-one, mp 129°–132° C.

Anal. Calcd. for $C_{25}H_{27}NO_3$: C, 77.07; H, 6.99; N, 3.60; Found: C, 76.85; H, 7.14; N, 3.45.

EXAMPLE 15

Preparation of trans-6-[2-[2-(4-fluorophenyl)-5-(1-methylethyl)-1H-pyrrol-1-yl]propyl]tetrahydro-4-hydroxy-2H-pyran-2-one The procedure of Example 1 was employed with the substitution in Step B of 2-aminopropanol in place of the ethanolamine. Therafter, the procedure of Steps C–E were followed to produce trans-6-[2-[2-(4-fluorophenyl)-5-(1-methylethyl)-1H-pyrrol-1-yl]propyl]tetrahydro-4-hydroxy-2H-pyran-2-one, mp 167°–169° C.

Anal. Calcd. for $C_{21}H_{26}FNO_3$: C, 70.17; H, 7.29; N, 3.90; Found: C, 70.06; H, 7.36; H, 7.36; N, 3.82.

EXAMPLE 16

Preparation of trans-tetrahydro-4-hydroxy-6-[2-[2-(2-methoxyphenyl)-5-(1-methylethyl)-1H-pyrrol-1-yl-ethyl]-2H-pyran-2-one The procedure of Example 1 was employed with the substitution of equimolar amounts of 2-methoxybenzaldehyde and 3-butene-2-one for the 1-(4-fluorophenyl)-2-propene-1-one and isobutyraldehyde in Step A of Example 1. Thereafter, the procedure of Steps B–E were followed to produce trans-tetrahydro-4-hydroxy-6-2-[2-(2-methoxyphenyl)-5-(1-methylethyl)-1H-pyrrol-1-yl-ethyl]-2H-pyran-2-one.

Anal. Calcd. for $C_{21}H_{27}NO_3$: C, 70.56; H, 7.61; N, 3.92; Found: C, 70.43; H, 7.66; N, 3.73.

EXAMPLE 17

Method 1

Step A: Preparation of 6-[2-[2-(4-fluorophenyl)-5(1-methylethyl)-1H-pyrrol-1-yl]ethyl]tetrahydro-4-tert-butyl dimethylsilyloxy-,trans-2H-pyran-2-one.

To a solution of 6-[2-[2-(4-fluorophenyl)-5-(1-methylethyl)-1H-pyrrol-1-yl]ethyl]-tetrahydro-4-hydroxy-trans-2H-pyran-2-one (0.52 g, 1.5 mmoles) and tert-butyldimethylchloro silane (0.27 g, 1.8 mmoles) in 5 ml of dry DMF was added imidazole (0.31 g, 4.5 mmoles) in one portion. The solution was stirred overnight at room temperature before partitioning between hexane (100 ml) and water (50 ml). The aqueous layer was extracted with two 50 ml portions of hexane. The combined hexane extracts were washed with $H_2O$ (2×25 ml), brine (25 ml), and dried (MgSo$_4$) Filtration through silica gel and concentration provided 0.7 g (100%) of the title compound. 80 MHz NMR (CDCl$_3$) δ 0.10 (S, 6H), 0.90 (S, 9H), 1.30 (d, J=Hz 6H), 1.4–1.8 (m, 4H), 2.48 (m, 2H), 2.95 (m, 1H), 3.9–4.3 (m, 3H), 5.85 (d, J=2 Hz 1H), 6.02 (d, J=2 Hz, 1H), 6.8–7.3 (m, 4H).

Step B: Preparation of 6-[2-[2-(4-fluorophenyl)-3,4-dichloro-5-(1-methylethyl)-1H-pyrrol-1-yl]ethyl]tetrahydro-4-hydroxy-trans-2H-pyran-2-one.

N-Chlorosuccinimide (6.48 mmoles, 0.87 g) was added in one portion to a stirred solution of 6-[2-[2-(4-fluorophenyl)-5-(1-methylethyl)-1H-pyrrol-1-yl]ethyl]-tetrahydro-4-tert-butyldimethylsilyloxy-trans-2H-pyran-2-one (1.49 g, 3.24 mmoles) in dry DMF (10 ml) cooled to 0° C. under dry nitrogen. The solution was stirred for one hour at 0° C. then warmed to room temperature for three hours. It was then diluted with water (50 ml) and extracted with ether (2×1000 ml). The ether extracts were diluted with 100 ml of hexane and washed with water (50 ml), 10% aq. NaHCO$_3$ (50 ml), 10% aq. NaHSO$_3$ (50 ml), brine (50 ml), and dried (MgSO$_4$). The crude product which remained after filtration and concentration was dissolved in tetrahydrofuran (15 ml) and treated with glacial acetic acid (0.75 ml, 13 mmoles) and tetrabutyl ammonium fluoride (9.72 ml of 1M THF solution). The solution was stirred for five hours, diluted with ethyl acetate (100 ml) and washed with saturated aq. NaHCO$_3$ (2×50 ml), brine (25 ml), and dried (MgSO$_4$). The residue which remained after filtration and concentration was flash chromatographed on silica gel eluting with 2:1 hexane-ethyl acetate. This provided 0.50 g (35%) of pure lactone. Recrystallization from ether-hexane provided colorless crystals mp 129°–131° C.

Anal. Calcd. for $C_{20}H_{22}FCL_2NO_3$: C, 57.98; H, 5.35; N, 3.38; Found: C, 58.24; H, 5.24; N, 3.39.

IR (KBr) v 3550, 2990, 1711, 1518, 12225, 1160, 1055, 851, 816 cm$^{-1}$ 200 MHz NMR (CDCL$_3$) δ 1.44 (d, J=7 Hz, 6H), 1.8 (m, 4H), 2.12 (d, J=3 Hz, 1H, —OH), 2.55 (m, 2H), 3.10 (M, 1H), 4.0 (M, 2H), 4.30 (M, 1H), 4.45 (M, 1H), 7.0–7.4 (M, 4H).

Method 2

Step A: Preparation of 2-(4-fluorophenyl)-5-(1-methylethyl)-3,4-dichloro-1H-pyrrole-1-propanenitrile.

N-Chlorosuccininide (practical, 105 g, 786.5 mmoles) was added in one portion to a stirred solution of 2-(4-fluorophenyl)-5-(1-methylethyl)-1H-pyrrole-1-propanenitrile (84 g, 327.7 mmoles) in 500 ml of dry dimethylformamide cooled to 0° C. under nitrogen. After stirring for 60 minutes at 0° C. and 90 minutes at 25° C., a further 8 g (60 mmoles) of N-chlorosuccininide were added. The solution was stirred a further 60 minutes before pouring into ether (3 liters) and washing with H$_2$O (3×500 ml), 10% aq. NaHSO$_3$ (300 ml), H$_2$O (300 ml), brine, and dried (MgSO$_4$). Flash chromatography on silica gel eluting with 10:1 hexane-ethyl acetate provided an oil which solidfied on standing. Recrystallization from isopropyl ether-hexane provided 96 g of colorless crystals mp 80°–82° C.

Anal. Calcd. for $C_{16}H_{15}CL_2FN_2$: C, 59.09; H, 4.65; N, 8.61; Found: C, 59.01; H, 4.56; N, 8.59.

IR (KBr) 2933, 2249, 1520, 1490, 1344, 1315, 1218, 848, 524 cm$^{-1}$. 100 MHz NMR (CDCl$_3$) δ 1.42 (d, J=7 Hz, 6H), 2.33 (t, J=7 Hz, 2H), 3.0 (sptet, J=7 Hz, 1H), 4.05 (t, J=7 Hz, 2H), 70–74 (M, 4H).

Employing the product of this step in the process described above in Step C of Example 1, provided 6-[2-[2-(4-fluorophenyl)-3,4-dichloro-5-(1-methylethyl)-1H-pyrrol-1-yl]-ethyl]tetrahydro-4-hydroxy-trans-2H-pyran-2-one.

EXAMPLE 18

Preparation of 6-[2-[2-(4-fluorophenyl)-3,4 dibromo-5-(1-methylethyl)-1H-pyrrol-1-yl]ethyl]tetrahydro-4-hydroxy-trans-2H-pyran-2-one Substitution of N-Bromosuccinimide for N-Chlorosuccinimide in Step B of Method 1, Example 17 provided a corresponding amount of the title compound mp 143° C.

Anal. Calcd. for $C_{20}H_{22}FBr_2NO_3$: C, 47.74; H, 4.41; N, 2.78; Br, 31.76; F, 3.77. Found: C, 47.52; H, 4.34; N, 2.84. Br, 31.75; F, 3.72.

IR (KBr) 3350, 2966, 1711, 1510, 1484, 1225, 1072, 847, 820 cm$^{-1}$. 200 MHz NMR (CDCl$_3$) δ 1.40 (d, J=7 Hz, 6H), 1.5–1.8 (m, 41t), 1.94 (brs, 1H, —OH), 2.58 (m, 2H), 3.13 (m, 1H), 4.0 (m, 2H), 4.31 (m, 1H), 4.47 (m, 1H), 7.0–7.3 (m, 4H).

EXAMPLE 19

Step A: Preparation of ethyl-2(1-(1-oxo-2,2,2-trifluoroethyl))-4-oxo-4-(4-fluorophenyl)-butyrate A solution of ethyl 1,1,1-trifluoroacetoacetate (14.6 ml, 0.1 mole) in dry DMF (100 ml) was added dropwise to a 0° C. suspension of hexane washed sodium hydride (0.106 mole) in 50 ml of dry DMF under nitrogen. When gas evolution was complete, a solution of α-bromo-4'-fluoroacetophenone (0.1 mole,) prepared as in J. Org. Chem. 29, 3459 (1964)) in 100 ml of dry DMF was added dropwise over 30 minutes. The mixture was allowed to warm slowly to 25° C. overnight. It was then quenched by addition of 6N HCl, poured into H₂O (1 liter) and extracted with ether (2×500 ml). The combined ether extracts were washed with H₂O (2×100 ml), brine (100 ml), and dried (MgSO₄). Flash chromatography on silica gel eluting with 5:1 hexane-ethylacetate provided 7 g of the title compound. IR (film) 3380, 1768, 1744, 1688, 1601, 1511, 1413, 1293, 1263, 1238, 1212, 1160, 1100, 1004, 841 cm$^{-1}$. 200 MHz NMR (CDCl₃) δ 1.29 (t, J=7 Hz, 3H), 3.75 (m, 2H), 4.26 (q, J=7 Hz, 2H), 4.55 (dd, J=4.7, 9.6 Hz, 1H), 7.21 (m, 2H), 8.02 (m, 2H)

Step B: Preparation of 2-(4-fluorophenyl)-5-trifluoromethyl-1H-pyrrole-1-propanenitrile.

A solution of ethyl-2-(1-(1-oxo-2,2,2-trifluoroethyl))-4-oxo-4-(4-fluorophenyl)-butyrate (5 g, 15.6 mmoles) in 110 ml of 5:5:1 acetic acid-water-conc. sulfuric acid was stirred and heated at reflux for four hours. The cooled solution was carefully poured into 400 ml of saturated aq. bicarbonate which was then extracted with ether (2×300 ml). The combined ether extracts were washed with saturated aq. bicarbonate (2×50 ml), brine (50 ml), and dried (MgSO₄). The crude diketone which remained after filtration and concentration (3 g) was dissolved in 20 ml of glacal acetic acid and 2 g (18 mmoles) of 3-aminopropanenitrile-½-fumarate were added. The solution was stirred and heated at reflux for five hours. The cooled solution was poured into 200 ml of saturated aq. bicarbonate and extracted with ether (2×200 ml). The combined ether extracts were washed with H₂O (2×50 ml), brine (50 ml), and dried (MgSO₄). Flash chromatography of the residue which remained after filtration and concentration provided 1.2 g (27%) of the title compound. IR (CDCl₃) 2258, 1611, 1570, 1478, 1337, 1172, 1106, 1064, 844 cm$^{-1}$. 200 MHz NMR (CDCL₃) δ 2.51 (t, J=7.3 Hz, 2H), 4.30 (t, J=7 Hz, 2H), 6.16 (d, J=3.8 Hz, 1H), 6.67 (d, J=3.8 Hz, 1H), 7.1-7.5 (m, 4H). Mass spectrum M/e 282, 263, 242, 229, 173.

Preparation of 6-[2-[2-trifluoromethyl-5-(4-fluorophenyl)-1H-pyrrol-1-yl]ethyl]tetrahydro-4-hydroxy-trans-2H-pyran-2-one.

Substitution of 2-(4-fluorophenyl)-5-trifluoromethyl-1H-pyrrole-1-propanenitrile for 2-(4-fluorophenyl)-3,4-dichloro-5-(1-methylethyl)-1H,-pyrrole-1-propanenitrile in Step C of Example 1 and following the procedures of Step C, D, and E resulted in a corresponding amount of the title compound as an oil.

Anal. Calcd. for C₁₈H₁₇F₄NO₃: C, 58.22; H, 4.61; N, 3.77. Found: C, 58.88; H, 5.07; N, 4.03.

IR (film) 3440, 2927, 1728, 156, 1477, 1342, 1266, 1230, 1160, 1101, 1060, 843, 782 cm$^{-1}$. 200 MHz NMR (CDCl₃) δ 1.3-2.1 (m, 4H), 2.34 (brs, 1H, —OH), 2.55 (m, 2H), 3.9-4.3 (m, 3H), 4.52 (m, 1H), 6.11 (d, J=3.8 Hz, 1H), 6.61 (dd, J=0.8, 3.8 Hz, 1H), 7.0-7.4 (m, 4H).

EXAMPLE 20

Preparation of (±)-N-(4-fluorobenzoyl)-N-[2-(2-ethyl)-1,3-dioxolanyl]valine

A solution of the methyl-2-bromo-3-methyl butyrate (4.6 g, 23.6 mmoles), 2-(1-(2-aminoethyl))-1,3-dioxolane (2.93 g, 25 mmoles) and triethylamine (3.5 ml, 25 mmoles) was stirred and heated in 25 ml of refluxing acetonitrile for 20 hours. The cooled solution was poured into ether (500 ml) and extracted 2M HCl (2×50 ml). The aqueous layer was made alkaline with 25% aq. NaOH and extracted with ethyl acetate (2×100 ml). The combined ethyl acetate extracts were washed with brine and dried (MgSO₄). Filtration and concentration provided 3 g of the title compound as liquid. 90 MHz NMR (CDCl₃) δ 0.9.3 (d, J=7 Hz, 6H), 1.70 (brs, 1H, —NH), 1.86 (m, 2H), 2.60 (m, 3H) 2.94 (d, J=6 Hz, 1H), 3.68 (s, 3H), 3.85 (m, 4H), 4.89 (t, J=4 Hz, 1H).

Preparation of ±-Methyl-N-(4-fluorobenzoyl)-N-[2-(2-ethyl)-1,3 dioxolanyl]valine.

To a stirred solution of Methyl-N-[2-(2-ethyl)-1,3-dioxolanyl]valine (3 g, 13 mmoles) and triethylamine (3.6 ml, 26 mmoles) in 20 ml of dichloromethane (CH₂CL₂) cooled to 0° C. was added a solution of 4-fluorobenzoyl chloride (1.65 ml, 14 mmoles) in 10 ml of (CH₂CL₂). The solution was stirred 60 minutes at 0° C. and 60 minutes at room temperature. It was then poured into ether and washed with water, saturated aq. bicarbonate, brine, and dried (MgSO₄). Flash chromatography on silica gel eluting with 1:1 hexane-ethyl acetate provided 3 g of the title compound. 90 MHz NMR (CDCl₃) δ 0.90, (brd, J=7 Hz, 6H), 1.8-2.5 (m, 3H), 3.45 (br, dd, J=6, 8 Hz, 1H), 3.72 (s, 3H), 3.80 (m, 6H), 4.80 (m, 1H), 6.9-7.5 (m, 4H).

Preparation of ±-N-(4-fluorobenzoyl)-N-[2-(2-ethyl)-1,3-dioxolyanyl]valine.

A solution of the methyl ester prepared above (1 g, 2.83 mmoles) and NaOH (0.4 g, 10 mmoles) in 10 ml of 4:1 CH₃OH—H—₂O was stirred and heated at reflux for three hours. The cooled solution was diluted with water and extracted with ether. The aqueous layer was acidified with 6M HCl and extracted with ethyl acetate. (2×). The combined ethyl acetate extracts were washed with brine and dried (MgSO₄). Filtration and concentration provided 0.96 g (2.8 mmoles) of acid. 90M Hz NMR (CDCl₃) δ 0.85 (m, 6H), 1.8 (m, 2H), 2.5 (m, 1H) 3.3-3.9 (m, 7H), 4.6 (m, 1H) 6.8-7.4 (m, 4H).

Preparation of dimethyl--[2-(2-ethyl)-1,3-dioxolanyl]dioxolanyl]-2-(4-fluorophenyl)-5-(1-methyl-ethyl)-1H-pyrrole-3,4-dicarboxylate Dimethyl acetylene dicarboxylate (1.3 ml, 10.6 mmoles) was added to a 25° C. solution of (±)-N-(4-fluorobenzoyl)-N-[2-(2-ethyl)-1,3-dioxolanyl]valine (1.8 g, 5.28 mmoles) dissolved in 10 ml of acetic anhydride. The evolution of carbon dioxide began immediately. The solution was stirred a further two hours, concentrated to remove excess acetylene and solvent, then filtered through silica gel. This provided 2 g of pyrrole as a solid which was recrystallized from isopropyl ether-hexane mp 143°-146° C.

Anal. Calcd. for C₂₂H₂₆FNO₆ C, 62.55; H, 6.20; N, 3.31. Found: C, 62.84; H, 6.23; N, 3.30.

IR (KBr) 1719, 1449, 1241, 1209, 1178, 945 cm$^{-1}$. 200 MHz NMR (CDCl₃) δ 1.35 (d, J=7 Hz, 6H), 1.80 (m, 2H), 3.18 (Septet, J=7 Hz, 1H), 3.56 (s, 3H), 1H), 3.7-4.0 (m, 6H), 3.83 (S, 3H), 4.64 (t, J=4 Hz, 1H), 7-7.3 (m, 4H).

Preparation of Dimethyl-1-(1-(3-oxopropyl))-2-(4-fluorophenyl)-5-(1-methylethyl)-1H-pyrrole-3.4-dicarboxylate A solution of dimethyl-1-[2-(2-ethyl)-1,3-dioxolanyl)-2-(4-fluorophenyl)-5-(1-methylethyl)-1H-pryrrole-3,4-dicarboxylate (0.5 g, 1.18 mmoles) and p-toluenesulfonic acid (0.23 g, 1.2 mmoles) in 12 ml of 5:1 acetone-water was stirred and heated at reflux for 48 hours. The cooled solution was concentrated, diluted with ether (200 ml), washed with saturated aq. bicarbonate (2×50 ml), brine (50 ml), and dried (MgSO₄). Flash chromatography on silica gel eluting with 4:1 hexane-ethyl acetate provided 0.4 g of pure aldehyde.

90 MHz NMR (CDCl₃) δ 1.35 (d, J=7 Hz, 6H), 2.61 (t, J=7 Hz, 2H), 3.18 (septet, J=7 Hz, 1H), 3.53 (s, 3H), 3.81 (s, 3H), 4.03 (t, J=7 Hz, 2H), 6.9–7.3 (M, 4H), 9.45 (s, 1H).

Preparation of Dimethyl-2-(4-Fluorophenyl)-5-(1-methylethyl)-1-[2-(tetrahydro-4-hydroxy-6-oxo-2H-pyran-2-yl)ethyl]-1H-pyrrole-3,4-dicarboxylate.

Substituion of dimethyl-1(1-(3-oxopropyl))-2-(4-fluorophenyl)-5-(1-methylethyl)-1H-pyrrole-3,4-dicarboxylate for 2-(4-fluorophenyl)-5-(1-methylethyl)-1H-pyrrole-1-propanol in Step C of Example 1 and following the procedures of Steps C, D, and E provided a corresponding amount of the title compound mp 167°–170° C.

Anal. Calcd. for C₂₄H₂₈FNO₇ C, 62.47; H, 6.12; N, 3.04. Found: C, 62.32; H, 5.87; N, 2.99.

IR (KBr) 2450, 2980, 1719, 1499, 1225, 1174, 1074, 811 cm⁻¹. 200 MHz NMR (CDCl₃) δ 1.34 (d, J=7 Hz, 6H), 1.57 (m, 4H), 2.40 (d, J=3 Hz, 1H), 2.56 (m, 2H), 3.16 (septet, J=7 Hz, 1H), 3.55 (s, 3H), 3.83 (s, 3H), 4.0 (m, 2H), 4.26 (m, 1H), 4.44 (m, 1H), 4.44 (m, 1H), 7.1–7.3 (m, 4H).

We claim:

1. A compound having the structural formula

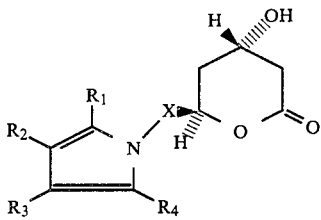

I wherein
X is
—CH₂—,
—CH₂CH₂—, or
—CH(CH₃)CH₂—;
R₁ is
1-naphthyl,
2-naphthyl,
cyclohexyl,
norbornenyl,
phenyl,
phenyl substituted by
fluorine,
chlorine,
hydroxy,
trifluoromethyl,
alkyl of from one to four carbon atoms,
alkoxy of from one to four carbon atoms,
alkanoyloxy of from two to eight carbon atoms,
2-, 3-, or 4-pyridinyl,
2-, 3-, or 4-pyridinyl-N-oxide,
R₂ and R₃ are independently
hydrogen,
chlorine,
bromine,
cyano,
trifluoromethyl,
phenyl,
alkyl of from one to four carbon atoms,
carboalkoxy of from two to eight carbon atoms,
R₄ is
alkyl of from one to four carbon atoms,
cyclopropyl,
cyclobutyl, or
trifluoromethyl;
or a corresponding lactone ring-opened dihydroxy acid derived therefrom, or a pharmaceutically acceptable salt thereof.

2. A compound in accordance with claim 1 wherein
X is —CH₂CH₂—;
R₁ is as defined in claim 1;
R₂ and R₃ are independently
hydrogen,
chlorine, or
bromine; and
R₄ is as defined in claim 1.

3. A compound in accordance with claim 1 wherein
X is —CH₂CH₂—;
R₁ is
phenyl,
phenyl substituted by
fluorine,
chlorine,
hydroxy,
trifluoromethyl,
alkyl of from one to four carbon atoms,
alkoxy of from one to four carbon atoms,
alkanoyloxy of from two to eight carbon atoms,
2-, 3-, or 4-pyridinyl,
2-, 3-, or 4-pyridinyl-N-oxide,
R₂ and R₃ are independently
hydrogen,
chlorine,
bromine; and
R₄ is alkyl of from one to four carbon atoms, or trifluoromethyl.

4. A compound in accordance with claim 1 wherein
X is —CH₂CH₂—;
R₁ is
phenyl, or
phenyl substituted by
fluorine,
chlorine,
hydroxy,
trifluoromethyl,
alkoxy of from one to four carbon atoms,
alkanoyloxy of from two to eight carbon atoms;
R₂ and R₃ are independently
hydrogen,
chlorine, or
bromine; and
R₄ is isopropyl or trifluoromethyl.

5. A compound in accordance with claim 1 having the name trans-6-[2-[3,4-dichloro-2-(4-fluorophenyl)-5-(1-methylethyl)-1H-pyrrol-1-yl]ethyl]tetrahydro-4-hydroxy-2H-pyran-2-one.

6. A compound in accordance with claim 1 having the name trans-6-[2-[3,4-dibromo-2-(4-fluorophenyl)-5-(1-methylethyl)-1H-pyrrol-1-yl]ethyl]tetrahydro-4-hydroxy-2H-pyran-2-one.

7. A compound in accordance with claim 1 having the name trans-6-[2-[2-(4-fluorophenyl)-5-(trifluoromethyl)-1H-pyrrol-1-yl)ethyl]tetrahydro-4-hydroxy-2H-pyran-2-one.

8. A compound in accordance with claim 1 having the name trans-dimethyl 2-(4-fluorophenyl)-5-(1- methylethyl)-1-[2-(tetrahydro-4-hydroxy-6-oxo-2H-pyran-2-yl)ethyl]-1H-pyrrole-3,4-dicarboxylate.

9. A compound in accordance with claim 1 having the name trans-6-[2-[2-(4-fluorophenyl-5-methyl-1H-pyrrol-1-yl]ethyl]tetrahydro-4-hydroxy-2H-pyran-2-one.

10. A compound in accordance with claim 1 having the name trans-6-[2-[2-(4-fluorophenyl-5-(1-methylethyl)-1H-pyrrol-1-yl]ethyl]tetrahydro-4-hydroxy-2H-pyran-2-one.

11. A compound in accordance with claim 1 having the name trans-6-[2-[2-cyclopropyl-5-(4-fluorophenyl)-1H-pyrrol-1-yl]ethyl]tetrahydro-4-hydroxy-2H-pyran-2-one.

12. A compound in accordance with claim 1 having the name trans-6-[2-[2-(1,1-dimethylethyl)-5-(4-fluorophenyl)-1H-pyrrol-1-yl]ethyl]tetrahydro-4-hydroxy-2H-pyran-2-one.

13. A compound in accordance with claim 1 having the name trans-tetrahydro-4-hydroxy-6-[2-[2-(2-methoxyphenyl)-5-methyl-1H-pyrrol-1-yl]ethyl]-2H-2-one.

14. A compound in accordance with claim 1 having the name trans-tetrahydro-4-hydroxy-6-[2-[2-(2-methoxyphenyl)-5-(1-methylethyl)-1H-pyrrol-1-yl]ethyl]-2H-pyran-2-one.

15. A compound in accordance with claim 1 having the name trans-tetrahydro-4-hydroxy-6-[2-[2-methyl-5-(1-naphthalenyl)-1H-pyrrol-1-yl]ethyl]-2H-pyran-2-one.

16. A compound in accordance with claim 1 having the name trans-6-[2-(2-bicyclo[2.2.1]hep-5-en-2-yl-5-methyl-1H-pyrrol-1-yl)ethyl]tetrahydro-4-hydroxy-2H-pyran-2-one.

17. A compound in accordance with claim 1 having the name trans-6-[2-[2-(4-fluorophenyl)-5-(1-methylphenyl)-1H-pyrrol-1-yl]propyl]tetrahydro-4-hydroxy-2H-pyran-2-one.

18. A pharmaceutical composition, useful as a hypocholesterolemic agent, comprising a hypocholesterolemic effective amount of a compound in accordance with claim 1 in combination with a pharmaceutically acceptable carrier.

19. A method of treating inhibiting cholesterol biosynthesis in a patient in need of such treatment by administering a pharmaceutical composition in accordance with claim 18.

* * * * *

UNITED STATES PATENT AND TRADEMARK OFFICE
Certificate

Patent No. 4,647,576

Patented: March 3, 1987

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bruce D. Roth, Ann Arbor, Michigan.

Signed and Sealed this Twenty-sixth Day of August 2003.

WILLIAM R. DIXON, JR.
*Supervisory Patent Examiner*
Art Unit 1600